United States Patent
Orihara

(10) Patent No.: US 7,854,700 B2
(45) Date of Patent: Dec. 21, 2010

(54) CAPSULE-TYPE ENDOSCOPE

(75) Inventor: Tatsuya Orihara, Hachioji (JP)

(73) Assignee: Olympus Corporation, Tokyo (JP)

( * ) Notice: Subject to any disclaimer, the term of this patent is extended or adjusted under 35 U.S.C. 154(b) by 1467 days.

(21) Appl. No.: 11/189,783

(22) Filed: Jul. 27, 2005

(65) Prior Publication Data
US 2006/0030752 A1    Feb. 9, 2006

(30) Foreign Application Priority Data
Aug. 4, 2004    (JP) .................. 2004-228170

(51) Int. Cl.
*A61B 1/06*    (2006.01)
(52) U.S. Cl. ....................... 600/160; 600/164
(58) Field of Classification Search .................. 600/109, 600/160, 153, 156, 158, 164, 176–177, 476
See application file for complete search history.

(56) References Cited

U.S. PATENT DOCUMENTS

| 4,778,247 | A  | * | 10/1988 | Carpenter ..................... 385/117 |
| 2003/0167000 | A1 | * | 9/2003 | Mullick et al. ............... 600/424 |
| 2003/0171652 | A1 | * | 9/2003 | Yokoi et al. ................. 600/160 |
| 2004/0225189 | A1 | * | 11/2004 | Kimoto et al. ............... 600/160 |
| 2004/0225190 | A1 | * | 11/2004 | Kimoto et al. ............... 600/177 |
| 2005/0043587 | A1 |   | 2/2005 | Fujimori et al. |
| 2005/0185299 | A1 | * | 8/2005 | Kislev et al. ................ 359/708 |

FOREIGN PATENT DOCUMENTS

| JP | 2003-325441 | 11/2003 |
| WO | WO 00/76391 A1 | 12/2000 |
| WO | WO 2004032621 A2 | 4/2004 |

\* cited by examiner

*Primary Examiner*—Thomas J Sweet
*Assistant Examiner*—Philip R Smith
(74) *Attorney, Agent, or Firm*—Arnold International; Bruce Y. Arnold

(57) ABSTRACT

A capsule-type endoscope includes a capsule, an objective optical system, an image pickup element, and at least one illumination light source having a light-emitting surface, and a transparent cover. In several embodiments of the capsule-type endoscope according to the present invention, an inner surface of the transparent cover is spherical within a field of view of the objective optical system so as to have a center of curvature, the center of curvature is offset from the optical axis of the objective optical system, and a specified condition is satisfied so as to avoid flare in the objective optical system caused when light from the one (or more) illumination light source(s) enters the entrance pupil of the objective optical system. In another embodiment, the inner surface of the transparent cover has the shape of an ellipsoid. Observation methods using the capsule-type endoscope are also disclosed.

25 Claims, 15 Drawing Sheets

US 7,854,700 B2

CAPSULE-TYPE ENDOSCOPE

This application claims the benefit under 35 U.S.C. §119 of JP 2004-228170, filed Aug. 4, 2004, the contents of which are hereby incorporated by reference.

BACKGROUND OF THE INVENTION

Conventional capsule-type endoscopes contain, for example, an objective optical system, an illumination means, an image pickup element, and a transmission means within a capsule-shaped shell. A cover member (hereinafter termed a transparent cover) that is generally spherical in shape and transparent within the field of view of the objective optical system seals these items within the capsule-shaped shell. Typically, a capsule-type endoscope having the above-discussed structure converts into signals in vivo images that are captured on a light-receiving surface of the image pickup element. These signals, of images that have been captured using light that has passed through the transparent cover and the objective optical system, are then transmitted externally by means of the transmission means. The transmitted signals are received by an external receiver device, and are then displayed on a display device for examination.

Capsule-type endoscopes as discussed above have a problem in that illumination light emitted from the illumination means is partly reflected by the inner surface of the spherical transparent cover and enters the entrance pupil of the objective optical system, which causes flare and significantly deteriorates the image contrast.

The inventions as disclosed, for example, in the following prior art patent documents have been proposed to prevent light that is reflected by the inner surface of the transparent cover from reaching the entrance pupil of the objective optical system and causing flare.

Japanese Laid-Open Patent Application 2003-325441 discloses a capsule-type endoscope in which the transparent cover has a spherical inner surface and the center of the entrance pupil of the objective optical system coincides with the center of curvature of this surface. Light that is emitted from the illumination means and reflected by the inner surface of the transparent cover is prevented from reaching the entrance pupil of the objective optical system, thus preventing flare. Also, Japanese Laid-Open Patent Publication 2003-501704 discloses an optical device in which the transparent cover has an ellipsoidal inner surface and multiple light sources that function as an illumination means are provided along a focal curve on the focal plane of the ellipsoid. Once again, the light that is emitted from the illumination means and reflected by the inner surface of the transparent cover is prevented from reaching the objective optical system and causing flare.

However, the capsule-type endoscope disclosed in Japanese Laid-Open Patent Application 2003-325441 requires that the illumination means be positioned around the objective optical system because of the structure that the center of the entrance pupil of the objective optical system coincides with the center of curvature of the inner surface of the transparent cover. This disadvantageously increases the size of the capsule-type endoscope.

As noted above, the light emitting elements that are used as the illumination means of the optical device disclosed in Japanese Laid-Open Patent Publication 2003-501704 must be located on the focal curve. Consequently, in order to provide sufficient room in which to mount these light-emitting elements, the transparent cover has to be increased in size, which requires that the size of the capsule-type endoscope itself be larger.

Furthermore, it is desired that the capsule-type endoscope described above provide a space for carrying a battery for ensuring sufficient operation time of the capsule-type endoscope or a tank for carrying a substance in liquid form. However, when an attempt is made to provide such a space in the prior art capsule-type endoscopes discussed above, the location of such a space must be such that no interference occurs between the objective optical system and the illumination means. This requirement tends to increase the size of the capsule-type endoscope.

BRIEF SUMMARY OF THE INVENTION

The present invention relates to a capsule-type endoscope that can be swallowed for an in vivo examination. The purpose of the present invention is to provide a capsule-type endoscope that can prevent light that is reflected by the inner surface of the transparent cover from causing flare in the objective optical system, even if the size of the capsule-type endoscope is decreased.

Another purpose of the present invention is to provide a capsule-type endoscope that can prevent light that is reflected by the inner surface of the transparent cover from causing flare in the objective optical system while simultaneously providing a sufficient space for mounting either a tank for carrying a substance in liquid form (such as a coloring agent or drug) for applying to a target region of a patient or a battery for increasing the operating time of the capsule-type endoscope.

BRIEF DESCRIPTION OF THE DRAWINGS

The present invention will become more fully understood from the detailed description given below and the accompanying drawings, which are given by way of illustration only and thus are not limitative of the present invention, wherein.

DETAILED DESCRIPTION

In the present invention, a capsule-type endoscope is provided with an image pickup unit that includes an objective optical system, an image pickup element, and an illumination light source. A transparent cover, that is transparent within the field of view of the objective optical system, seals these components within an external surface. At least within the field of view of the objective optical system, the inner surface of the transparent cover is spherical so as to have a center of curvature, the optical axis of the objective optical system is offset from the center of curvature of the transparent cover, and the following Condition (1) is satisfied:

$$0.01 < L1/R \tan\theta < 0.5 \qquad \text{Condition (1)}$$

where

L1 is the distance between the center of curvature of the inner surface of the transparent cover and the optical axis of the objective optical system;

R is the radius of curvature of the inner surface of the transparent cover; and

θ is the half-field angle of the objective optical system.

It is preferred in the capsule-type endoscope of the present invention that the light emitting surface(s) of the light sources that form an illumination means are positioned in a manner such that the light emitting surface(s) does (do) not overlap an image of the entrance pupil of the objective optical system when light rays are projected onto a plane Qm by being reflected by the inner surface of the transparent cover, where the plane Qm is defined as the plane containing the light emitting surface(s) of the illumination means.

Furthermore, the capsule-type endoscope of the present invention is characterized by the fact that the optical axis of the objective optical system is non-orthogonal to the tangential plane of the inner surface of the transparent cover where it intersects same (hereinafter referred to simply as 'not orthogonal to the inner surface of the transparent cover'), and at least one of the components of the image pickup unit is tilted so as to be non-orthogonal to the optical axis of the objective optical system or is de-centered relative to other components of the image pickup unit.

The present invention provides a capsule-type endoscope that can prevent light that is reflected by the inner surface of the transparent cover from causing flare in the objective optical system, even in the case where the capsule size is reduced or while ensuring that there exists a space for mounting either a tank for carrying a substance in liquid form or a battery for increasing the operating time of the capsule-type endoscope. The present invention will first be discussed in general terms with reference to FIGS. 1(a) and 1(b).

Figures 1A, 1B:
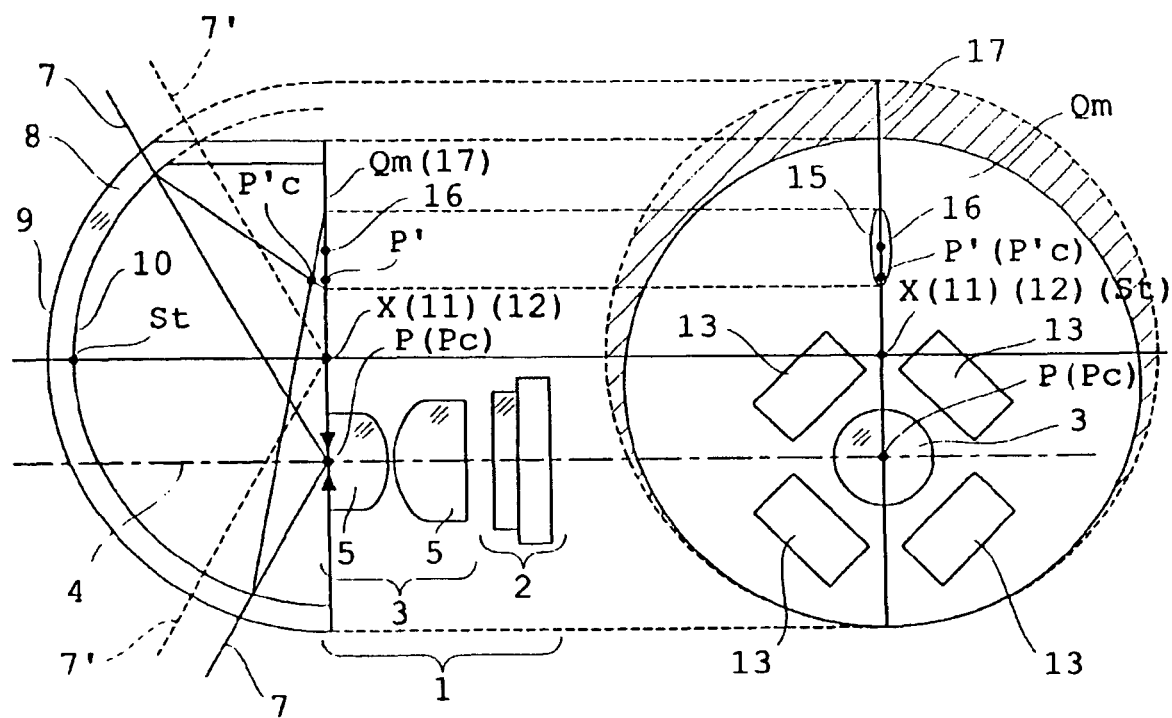
FIGS. 1(a) and 1(b) are cross-sections of a front portion of a capsule-type endoscope as viewed from the side and front, respectively.

FIGS. 1(a) and 1(b) are sectional illustrations of a capsule-type endoscope according to one embodiment of the present invention as viewed from the side and front, respectively. In FIGS. 1(a) and 1(b), item 4 is the optical axis of the objective optical system 3, and St is the vertex of the inner surface 10 of the transparent cover 8. Here, the vertex St is a point on the inner surface 10 of the transparent cover 8 at which the distance between two points Gn and En is largest. Gn is a point on the inner surface 10 of the transparent cover 8 and En is the intersection of a normal from the point Gn to a plane that is orthogonal to the optical axis and tangential to the most object side surface (surface being nearest to an object) of the objective optical system 3. Item 9 is the outer surface of the transparent cover, P(Pc) is the center of the entrance pupil of the objective optical system 3, and P'c is the point of intersection of hypothetical light rays if emitted from the center Pc of the entrance pupil and reflected by the inner surface 10 of the transparent cover 8. Qm is as defined above, namely, the plane containing the light emitting surface(s) of the illumination means, X is the point of intersection of a line drawn from the vertex St of the inner surface of the transparent cover normal to the plane Qm, and P' is the point of intersection of a normal line drawn from the point P'c to the plane Qm. Region 15 (herein termed the reflected image of the entrance pupil of the objective optical system) is defined by the outer limit of hypothetical light rays emitted from the center of the entrance pupil of the objective optical system 3, when such hypothetical light rays are then reflected by the inner surface 10 of the transparent cover 8 so as to be incident onto the plane Qm.

The capsule-type endoscope shown in FIGS. 1(a) and 1(b) is an embodiment of the present invention in which the inner surface 10 of the transparent cover 8 is spherical. In the capsule-type endoscope shown in FIGS. 1(a) and 1(b), the objective optical system 3 is provided with the center Pc of its entrance pupil on a line 17 (in the plane Qm) that passes through the center of curvature 11 of the inner surface 10 of the transparent cover 8 and is orthogonal to the optical axis 4 of the objective optical system 3. In FIG. 1(a), the dashed lines 7', 7' define the outer limits of the field of view of a prior art capsule-type endoscope in which the center Pc of the entrance pupil of the objective optical system 3 coincides with the center of curvature 11 of the inner surface 10 of the transparent cover 8. On the other hand, the solid lines 7, 7 define the outer limits of the field of view of the objective optical system 3 when the center Pc of the entrance pupil of the objective optical system 3 is provided at a point that is laterally offset from the center of curvature 11, and when the above Condition (1) is satisfied.

The outer surface 9 of the transparent cover 8 has its center of curvature at 12. In the capsule-type endoscope shown in FIGS. 1(a) and 1(b), the centers of curvature 11 and 12 of the inner and outer surfaces 10 and 9 of the transparent cover 8 coincide.

Satisfying Condition (1) above enables the cross-section size of the capsule to be reduced by the area indicated by the shaded part in FIG. 1(b) while maintaining the same field of view of the objective optical system as in prior art capsule-type endoscopes.

Further, the light emitting surface(s) of the illumination means 13 does (do) not overlap the reflected image 15 of the entrance pupil of the objective optical system 3 on the plane Qm, as can be seen in the capsule-type endoscope shown in FIGS. 1(a) and 1(b). Thus, illumination light emitted from the illumination means 13 and reflected by the inner surface of the transparent cover 8 does not reach the entrance pupil of the objective optical system 3, thereby preventing flare.

When the upper limit of Condition (1) above is not satisfied, the objective optical system 3 is too close to the vertex St of the inner surface 10 of the transparent cover 8, failing to reserve a space for providing the illumination light source. On the other hand, when the lower limit of Condition (1) is not satisfied, the objective optical system 3 is too far away from the vertex St of the inner surface 10 of the transparent cover 8, unfavorably increasing the entire capsule length.

It is preferred in the capsule-type endoscope of the present invention that the objective optical system be provided in a manner such that its optical axis is non-orthogonal to the inner surface of the transparent cover, and at least one of the components of the image pickup unit is tilted so as to be non-orthogonal to the optical axis of the objective optical system or is de-centered relative to other components of the image pickup unit.

Figure 2:
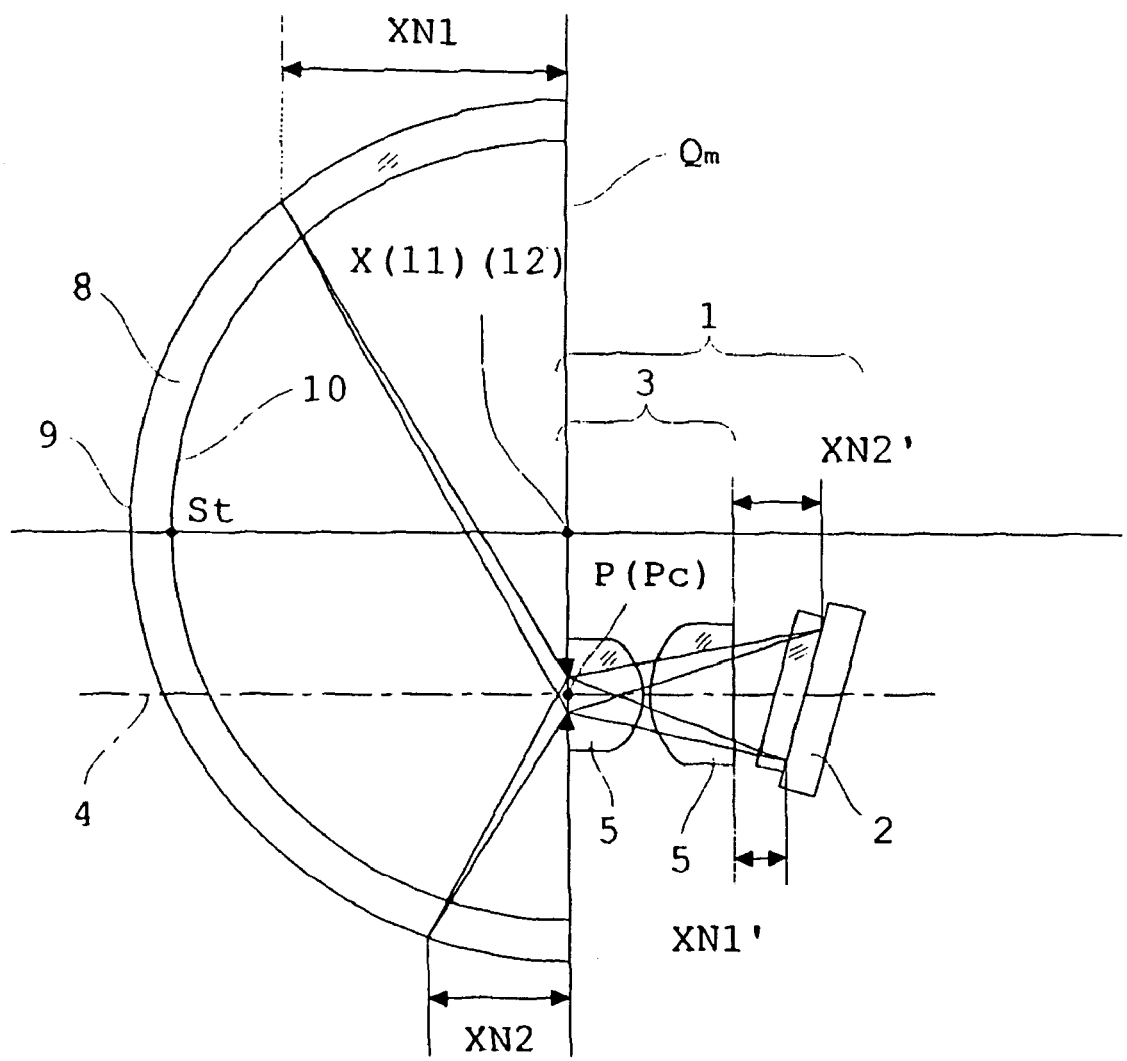
FIG. 2 is a cross-section of a front portion of a capsule-type endoscope as viewed from the side that shows forming images of object points located on the outer surface of the transparent cover at the outer limits of the field of view of the objective optical system.

FIG. 2 is an illustration to explain another important feature of the capsule-type endoscope of the present invention. It shows object points on the outer surface 9 of the transparent cover 8 at the outer limits of the field of view of the objective optical system 3 (in a cross section that contains the optical axis 4 of the objective optical system 3 and the vertex St of the inner surface 10 of the transparent cover 8) being imaged by the objective optical system 3.

Unlike conventional endoscopes, the capsule-type endoscope of the present invention does not have a mechanism for sending air into the organ during observation/diagnosis. Therefore, the digestive tract (i.e., the usual passageway of the capsule endoscope) is presumably contracted and thus at least partially blocks the field of view of the objective optical system of the capsule-type endoscope. In addition, when the capsule is moved within a living body (hereinafter sometimes referred to simply as a 'body') by means of peristaltic motion of a tubular organ, the capsule is subjected to uniform pressure by the inner wall of the tubular organ. The inner wall of the tubular organ is in contact with the outer surface of the capsule in the most stable manner and the inner wall of the tubular organ also surrounds the outer surface of the transparent cover along its curved surface. Therefore, it is desired that the image pickup unit be able to focus on an object point that is located on the outer surface 9 of the transparent cover 8.

The image pickup unit 1 may be formed of an objective optical system 3 having lens components 5, 5 (which, as shown, may each consist of a lens element), a diaphragm (not shown), a lens frame (not shown), a spacing ring (not shown), an image pickup element 2, and an image pickup element frame (not shown).

As shown in FIG. 2, when the objective optical system 3 is positioned with the center of its entrance pupil shifted from the centerline of the capsule so that the optical axis of the objective optical system 3 is non-orthogonal to the inner surface of the transparent cover 8, the distance between the most object-side surface of the objective optical system 3 and the outer surface 9 of the transparent cover 8 varies, depending on the direction of viewing. This results in a shifting of the image position for each object point. Therefore, if the image pickup surface of the image pickup element 2 is orthogonal to the optical axis of the objective optical system as in prior art capsule-type endoscopes, an object of interest, such as the inner surface of a tubular organ that is in contact with the outer surface of the transparent cover 8, will have a portion that is not properly focused onto the surface of the image pickup element, and this will cause difficulty in observation.

In the capsule-type endoscope shown in FIG. 2, the image pickup element 2 is tilted so as to be non-orthogonal to the optical axis of the objective optical system 3 in such a manner that the image pickup surface is positioned at the image positions XN1', XN2' that correspond to the distances XN1, XN2 between the most object-side surface of the objective optical system 3 and the outer surface 9 of the transparent cover 8. In this way, focal shifts as a result of differences in the object point distance to the outer surface 9 of the transparent cover 8 in different viewing directions is corrected. In this manner, a small-sized, capsule-type endoscope that allows for clear observations of an object, such as the inner wall of a tubular organ, that is in contact with the outer surface 9 of the transparent cover 8 can be provided.

In lieu of, or in addition to, the image pickup unit being tilted as shown in FIG. 2, at least one of the components of the image pickup unit other than the image pickup element can be de-centered relative to other components of the image pickup unit. In this way, focal shifts as a result of differences in the object distance to the outer surface 9 of the transparent cover 8 in different viewing directions can be similarly corrected and clear images can be obtained.

Various embodiments of the capsule-type endoscope of the present invention will now be described in detail with reference to the drawings.

Embodiment 1 and Two Possible Modifications

Figures 3A, 3B:
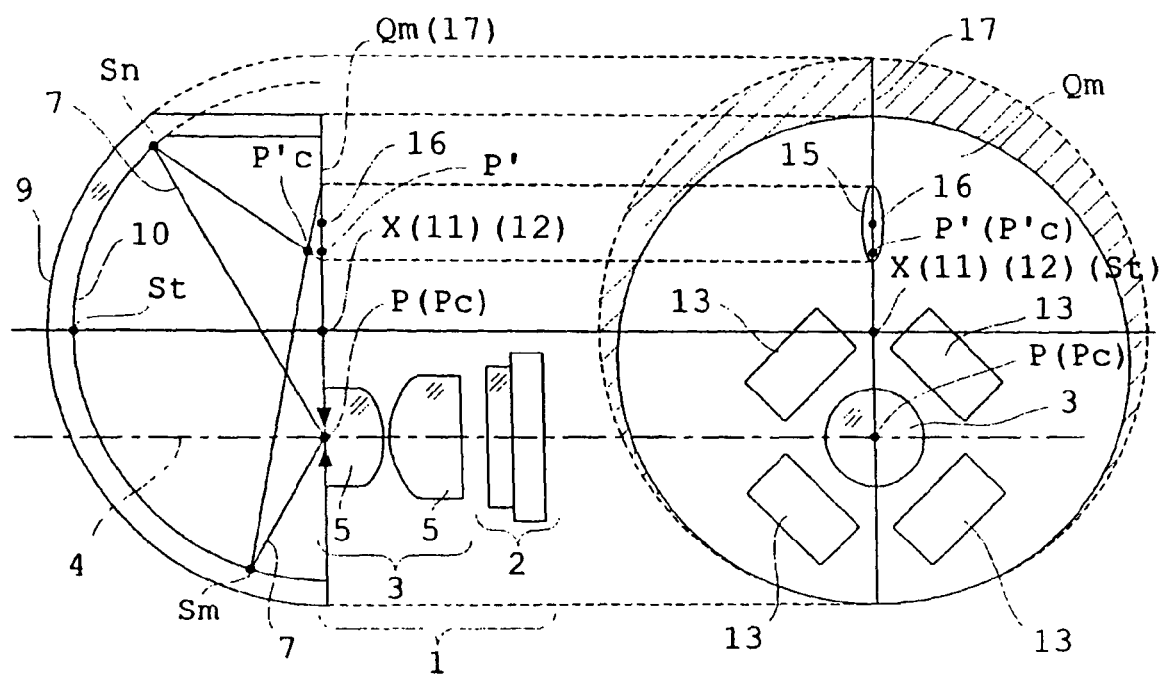
FIGS. 3(a) and 3(b) are illustrations which relate to Embodiment 1 of the present invention, with FIG. 3(a) being a cross-section of a front portion of the capsule-type endoscope as viewed from the side, and FIG. 3(b) being a cross-section of the front portion of the capsule-type endoscope as viewed from the front.

FIGS. 3(a) and 3(b) are illustrations which show the front portion of a capsule-type endoscope according to Embodiment 1 of the present invention, with FIG. 3(a) being a cross-section of a front portion of the capsule-type endoscope as viewed from the side, and FIG. 3(b) being a cross-section of a front portion of the capsule-type endoscope as viewed from the front. Like items in the drawings have been similarly numbered throughout the drawings. The illumination means 13 may be formed of semiconductor-chip-type, light emitting diodes (hereinafter termed LEDs), that are provided at different positions within the capsule, and the capsule-type endoscope is provided with a cover that is transparent within the field of view of the objective optical system 3 and that seals the capsule. The entrance pupil of the objective optical system 3 coincides with the most object-side surface of the lens components 5, 5 that form the objective optical system 3. Furthermore, the entrance pupil plane is on the same plane as the plane Qm that contains the light emitting surface(s) of the illumination means 13. A power supply battery and a transmission antenna for transmitting information, such as images, to a separate receiver device (not shown) are provided behind (i.e., on the image side of) the objective optical system 3.

As in FIG. 1, the inner surface 10 of the transparent cover 8 is spherical, and the center of curvature 11 of the inner surface 10 of the transparent cover 8 is on a line 17 that passes through the center Pc of the entrance pupil of the objective optical system 3 and is orthogonal to the optical axis 4 of the objective optical system 3. The lines 7, 7 are drawn through the center of the entrance pupil of the objective optical system 3 so as to pass through the points Sm and Sn that are located on the inner surface 10 of the transparent cover and these lines define the outer limits of the field of view of the objective optical system 3.

As mentioned above, the size of the capsule can be reduced relative to that of prior art capsule-type endoscopes by offsetting the optical axis of the objective optical system from the axial center of the capsule. In this embodiment, the offset amount is 0.76 mm for a prior art transparent cover having an outer diameter of 5.6 mm. In this way, the cross-sectional area of the capsule can be reduced (as shown by the hatched area illustrated in FIG. 3(b)) and the outer diameter of the capsule's cylindrical surface can be reduced from 5.6 mm to 5.0 mm. The reflected image range 15 of the entrance pupil of the objective optical system is defined herein as the intersection points with the plane Qm of hypothetical light rays that emerge from the center Pc of the entrance pupil of the objective optical system at the outer limits of the field of view of the objective optical system and are then reflected by the inner surface of the transparent cover onto the plane Qm.

The reflected image range 15 (defined above) may be determined by reverse ray tracing light rays entering the center Pc of the entrance pupil of the objective optical system 3 from points on the inner surface of the transparent cover 8 that are at the outermost periphery of the field of view. In other words, in FIG. 3(a), the reflected image range 15 of the entrance pupil of the objective optical system 3 is determined by the light rays 7 that form the outer limits of the field of view of the objective optical system, if such rays were to be reversed, reflected by the inner surface 10 of the transparent cover 8, and were then to be incident onto the plane Qm.

In the capsule-type endoscope of Embodiment 1, four LEDs comprise the illumination means 13 and these LEDs are provided outside the reflected image range 15 of the entrance pupil of the objective optical system 3. In addition, none of the optical axes of the LEDs is orthogonal to the inner surface 10 of the transparent cover 8. The optical axis of each of the four LEDs passes through the center of its light-emitting surface and is orthogonal to the light-emitting surface. When multiple light emitting surfaces form the illumination means 13, and when these surfaces do not lie in the same plane Qm, the objective optical system 3 and each LED are positioned to satisfy Condition (1) above within the respective planes containing the light emitting surfaces of the illumination means 13.

With the capsule-type endoscope of Embodiment 1 having the structure discussed above, a capsule-type endoscope can be provided that is reduced in size relative to that of prior art capsule-type endoscopes, while ensuring the same field of view. Moreover, light emitted from the illumination means 13 and reflected by the inner surface of the transparent cover 8 can be prevented from entering the entrance pupil of the objective optical system 3. Therefore, flare can be prevented so as to allow for observation of clear images.

Figures 4A, 4B:
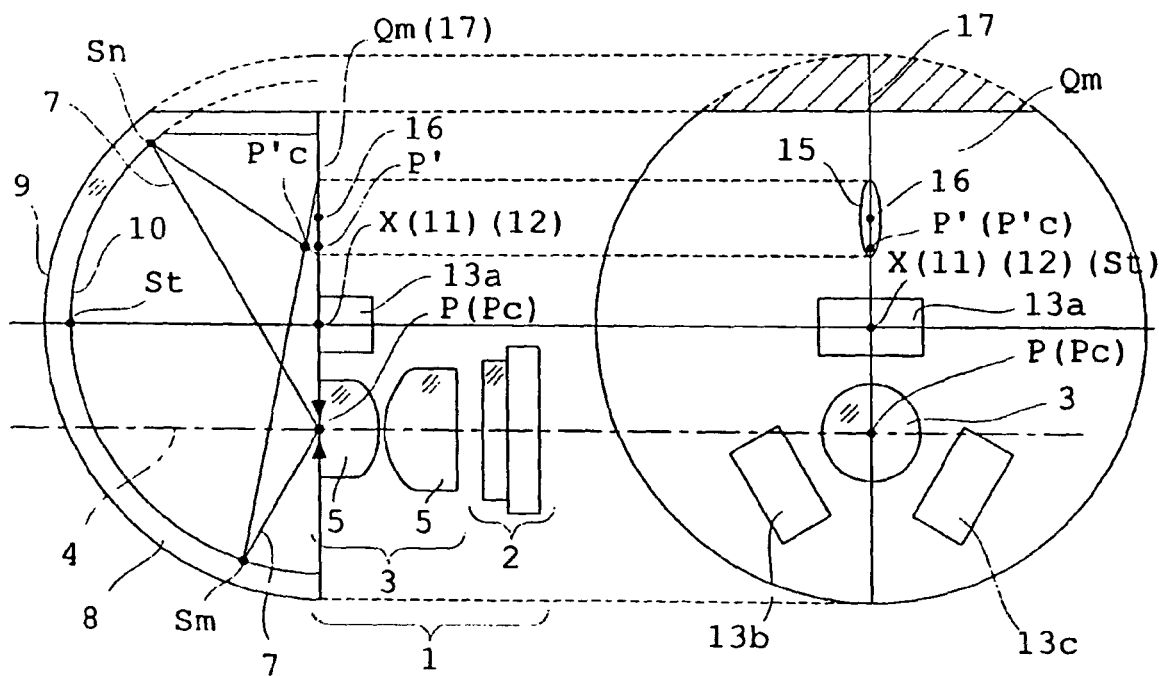
FIGS. 4(a) and 4(b) relate to a first possible modification to Embodiment 1 of the present invention, with FIG. 4(a) being a cross-section of a front portion of the capsule-type endoscope as viewed from the side, and FIG. 4(b) being a cross-section of a front portion of the capsule-type endoscope as viewed from the front.

FIGS. 4(a) and 4(b) show a first possible modification to Embodiment 1, with FIG. 4(a) being a cross-section of a front portion of the capsule-type endoscope as viewed from the side, and FIG. 4(b) being a cross-section of a front portion of the capsule-type endoscope as viewed from the front. In the capsule-type endoscope of the modification to Embodiment 1 shown in FIGS. 4(*a*) and 4(*b*), one of the illumination light sources (such as the illumination light source 13a) is provided with its optical axis orthogonal to the inner surface 10 of the transparent cover 8. This modification to Embodiment 1 will now be discussed in comparison with a prior art capsule-type endoscope having a transparent cover diameter of 8.3 mm, as indicated by the dashed lines in FIG. 4(*a*). By offsetting the optical axis of the objective optical system from the axial center of the capsule a distance of 1.7 mm, the outer diameter of the capsule's cylindrical surface can be reduced from 8.3 mm to 7.4 mm. As before, the lines 7, 7 are drawn through the center of the entrance pupil of the objective optical system 3 so as to pass through the points Sm and Sn that are located on the inner surface 10 of the transparent cover 8 and that define the outer limits of the field of view of the objective optical system 3.

Figures 5A, 5B:
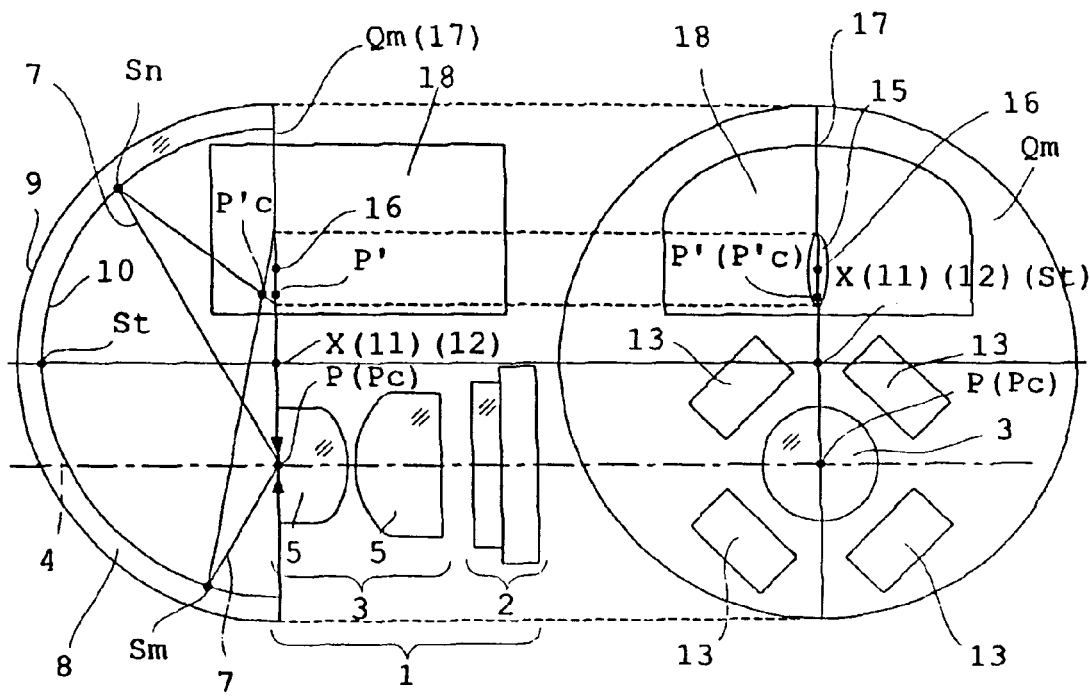
FIGS. 5(a) and 5(b) relate to a second possible modification to Embodiment I of the present invention, with FIG. 5(a) being a cross-section of a front portion of the capsule-type endoscope as viewed from the side, and FIG. 5(b) being a cross-section of a front portion of the capsule-type endoscope as viewed from the front.

FIGS. 5(*a*) and 5(*b*) show a second possible modification to Embodiment 1, with FIG. 5(*a*) being a cross-section of a front portion of the capsule-type endoscope as viewed from the side, and FIG. 5(*b*) being a cross-section of a front portion of the capsule-type endoscope as viewed from the front. With the second possible modification to Embodiment 1 as shown in FIGS. 5(*a*) and 5(*b*), a space for mounting other members can be obtained without increasing the capsule size as compared with a prior art capsule-type endoscope. As a result, a capsule-type endoscope can be obtained that has space for a tank 18 for carrying a substance in liquid form while preventing light that is reflected by the inner surface of the transparent cover 8 from entering the entrance pupil of the objective optical system and causing flare. Instead of a tank for a carrying a substance in liquid form being mounted in the space for mounting other members, one of a battery to extend the operation time of the capsule endoscope, a wireless transmission/reception means, or a capacitor can be mounted. Other structures remain the same as for the capsule-type endoscope shown in FIGS. 33(*a*) and 33(*b*), and therefore further explanation will be omitted. The capsule-type endoscope of this modified embodiment allows for providing one of a substance in liquid form (such as a coloring agent or a drug) to a lesion, an extended operating time of the image pickup system, improved reliability of the wireless communications, or another power source (such as a capacitor) within a small-sized, capsule-type endoscope.

In the case where a tank for delivery of a substance in liquid form to a lesion is provided, the capsule endoscope exterior is provided with a nozzle for spraying the substance in liquid form. When a possible lesion is found by observing the inner wall of an organ that is in the field of view of the objective optical system while the capsule-type endoscope moves along within tubular organs such as organs of the digestive tract, a substance such as a coloring agent can be sprayed on the region through the nozzle. Therefore, a jet orifice of the nozzle is directed in the viewing direction, and the field of view of the objective optical system and the spray range of the nozzle should overlap. It is further desired that the nozzle be at a position that does not obscure the observation of a target region within the field of view.

Figure 6:
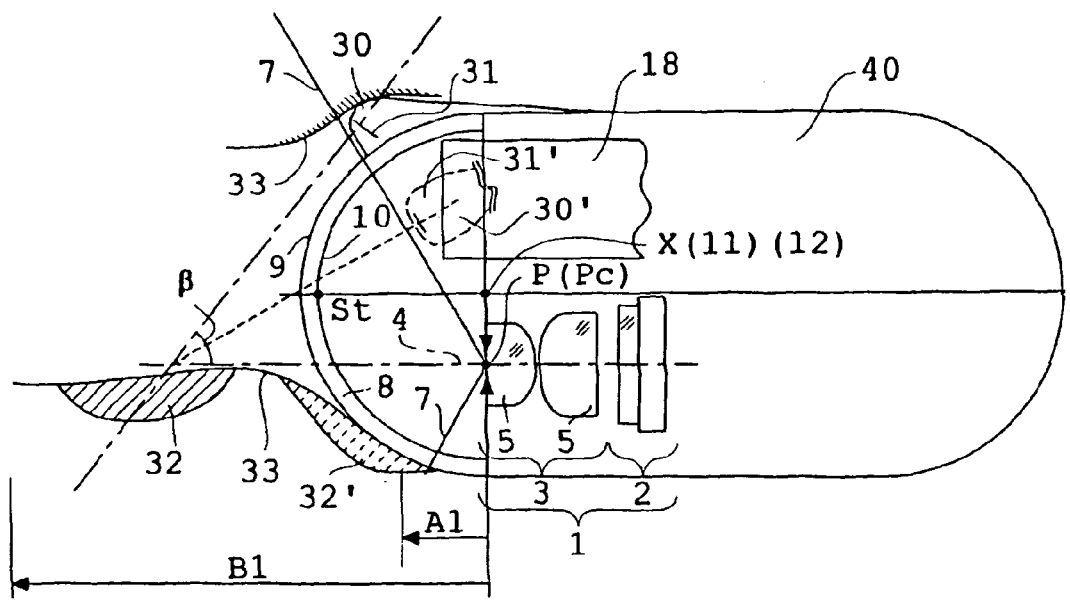
FIG. 6 shows the positional relationships of the field of view of the objective optical system of a capsule-type endoscope, a jet orifice of a nozzle for spraying a substance in liquid form onto a target region, and the observation target region of the capsule-type endoscope according to the second possible modification to Embodiment 1 shown in FIGS. 5(a) and 5(b)

FIG. 6 is an illustration to show the positional relationships within the outer limits 7, 7 of the field of view of the objective optical system 3, a jet orifice of a nozzle 30 for applying a substance in liquid form, and an observation target region 32 of the capsule-type endoscope 40 of the modification to Embodiment 1 shown in FIGS. 5(*a*) and 5(*b*). Presumably, the inside of a tubular organ (such as the small intestine, though which the capsule-type endoscope 40 passes) contacts the peripheral portion of the transparent cover of the capsule-type endoscope 40. The capsule-type endoscope 40 is moved along through the tubular organ by means of the peristaltic motion of the tubular organ. Therefore, a part of the outer surface 9 of the transparent cover 8 is in contact with the inner wall 33 of the tubular organ and is within the field of view of the objective optical system 3.

The capsule-type endoscope shown in FIG. 6 is designed to expand the inner wall 33 of the tubular organ through which it passes for enabling a substance in liquid form to be sprayed onto the inner wall of the tubular organ. As shown in FIG. 6, which illustrates a cross-section of the capsule-type endoscope as viewed from the side, a jet orifice 31 of the nozzle 30 is provided outside the field of view of the objective optical system 3. In addition, if the angle β between the centerline of the jet orifice 31 and the optical axis 4 of the objective optical system 3 is made to lie in the range of 15° to 75°, the nozzle and jet orifice can be relatively near the optical axis of the objective optical system 3, as indicated by a nozzle 30' and a jet orifice 31' as shown in dashed lines. A substance in liquid form is pushed out from the tank 18 to the nozzle 30 by a spray control device associated with the tank. Liquid is ejected from the jet orifice 31 and sprayed onto the observation target region 32 within a region delimited by the mid-point and the far point of the depth of field.

If the angle β is smaller than 15°, the spray target region and the jet orifice 31 are too distant from each other; therefore the liquid substance will be sprayed onto an excessively large region, thereby failing to put sufficient spray per unit area on the target region. On the other hand, if β is larger than 75°, the spray target region and the jet orifice 31 are too close to each other; therefore, the spray will contact the outer surface 9 of the transparent cover 8 and portions of the target region will be insufficiently sprayed.

The nozzle shown in FIG. 6 is provided outside of the field of view of the objective optical system. However, the nozzle can be positioned so that at least a portion of the nozzle is within the field of view, if this does not interfere with the observation of a target region within the field of view. This is actually the preferred situation since it allows the spraying of the substance in liquid form to be observed within the field of view. In such a case, it is desired that the nozzle surface be processed so as to reduce the amount of light reflected by the nozzle. Alternately, a light absorbing black coating can be applied to the nozzle surface so that illumination light that would otherwise be reflected by the nozzle and cause flare within the field of view is minimized.

Figure 7:
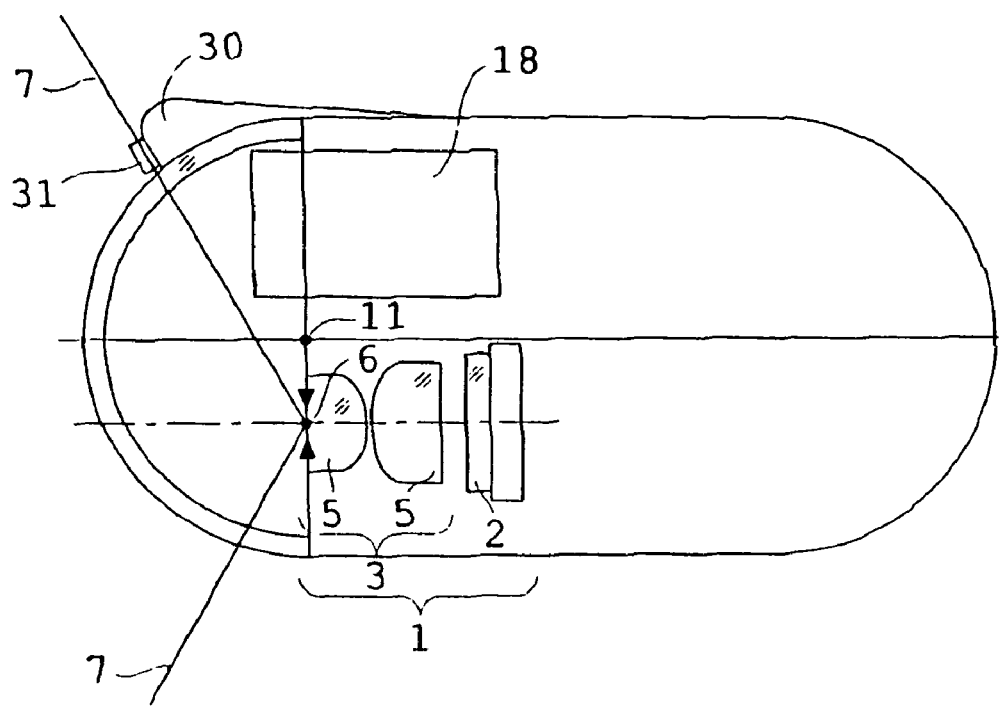
FIG. 7 shows an embodiment of the capsule-type endoscope in which the jet orifice of a nozzle is positioned within the field of view of the objective optical system.
Figure 22A:
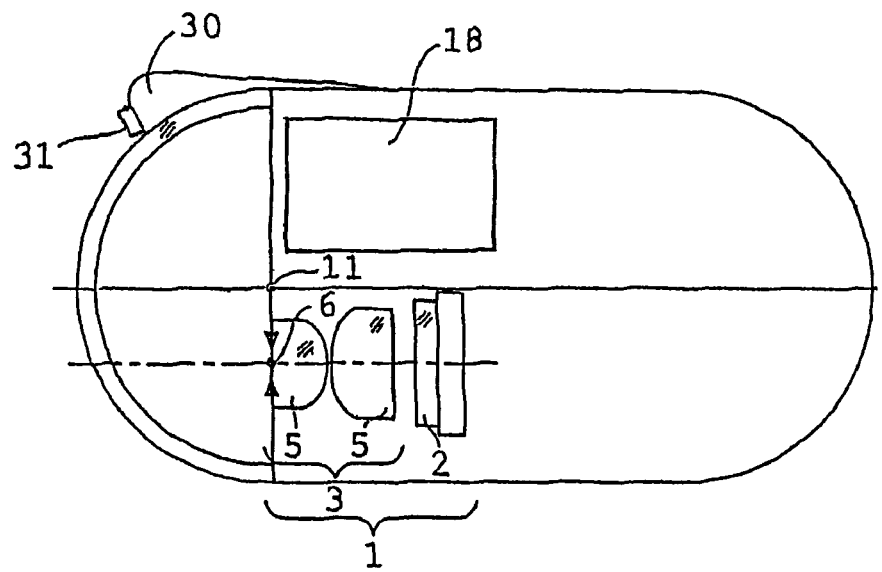
FIGS. 22(a) and 22(b) show a capsule-type endoscope in which a nozzle and tank for carrying a substance in liquid form are constituted as a unit that is detachably attached to the capsule-type endoscope.
Figure 22B:
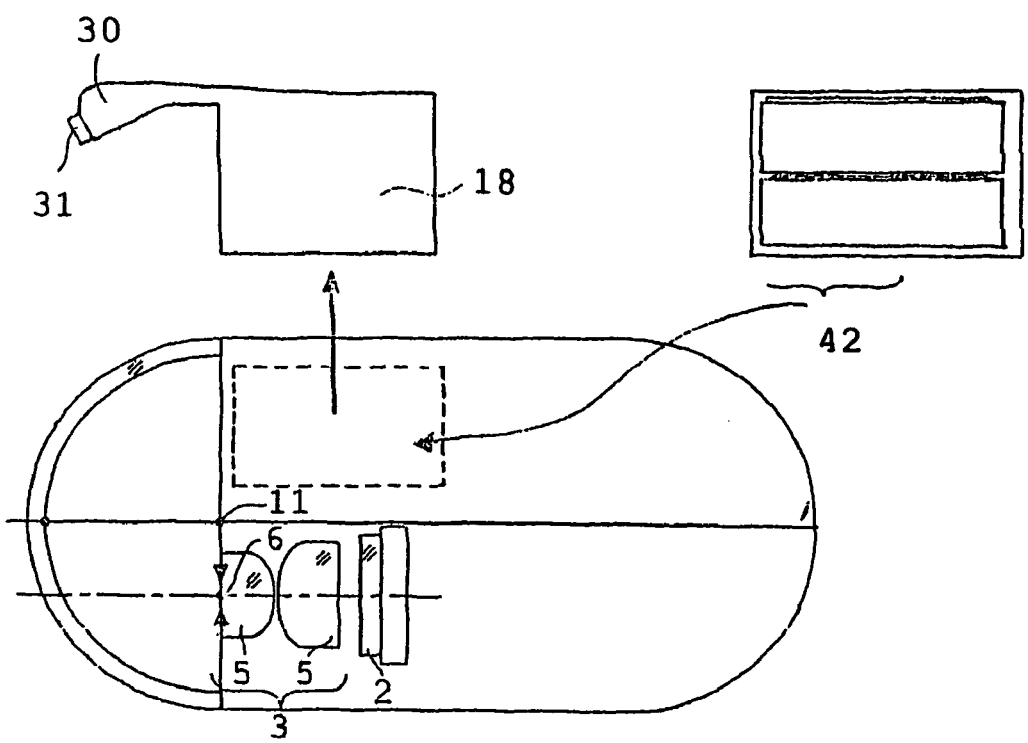

FIG. 7 shows an embodiment of the capsule-type endoscope in which the jet orifice of the nozzle is positioned within the field of view of the objective optical system. The jet orifice 31 of the nozzle 30 of the capsule-type endoscope shown in FIG. 6 is provided at a position that is within the field of view of the objective optical system 3 and where it does not interfere with the observation of a target region within the field of view. As shown in FIGS. 22(*a*) and 22(*b*), the nozzle 30 and tank 18 can be formed as a unit that is detachably attachable to the capsule-type endoscope. In this way, the tank may be easily filled with a substance in liquid form, such as a solution. Further, when delivery of a substance to a target region is not required, the tank can be removed and, in its place, an extra power unit 42 can be mounted for prolonged observations.

A capsule-type endoscope may be provided with a delivery tube having a puncture needle at one end that can be used when a substance in liquid form (such as a coloring agent or a drug) is desired to be injected into a living tissue. In such a case, the puncture needle is penetrated into the living tissue at a position that is within the field of view of the objective optical system, and the substance in liquid form is injected via the delivery tube from the tank within the capsule. To accomplish this, a projection port for the puncture needle should be positioned within the field of view of the objective optical system so that the tip of the puncture needle can be observed before the tip of the puncture needle is inserted into the living tissue. This is to ensure that the puncture needle tip does not puncture at an unintended point and to ensure that the puncture needle tip does not extend entirely through, and thus beyond, the intended living tissue. A similar precaution can be taken for a puncture needle to be inserted into living tissue for collecting biopsy samples.

Figure 8:
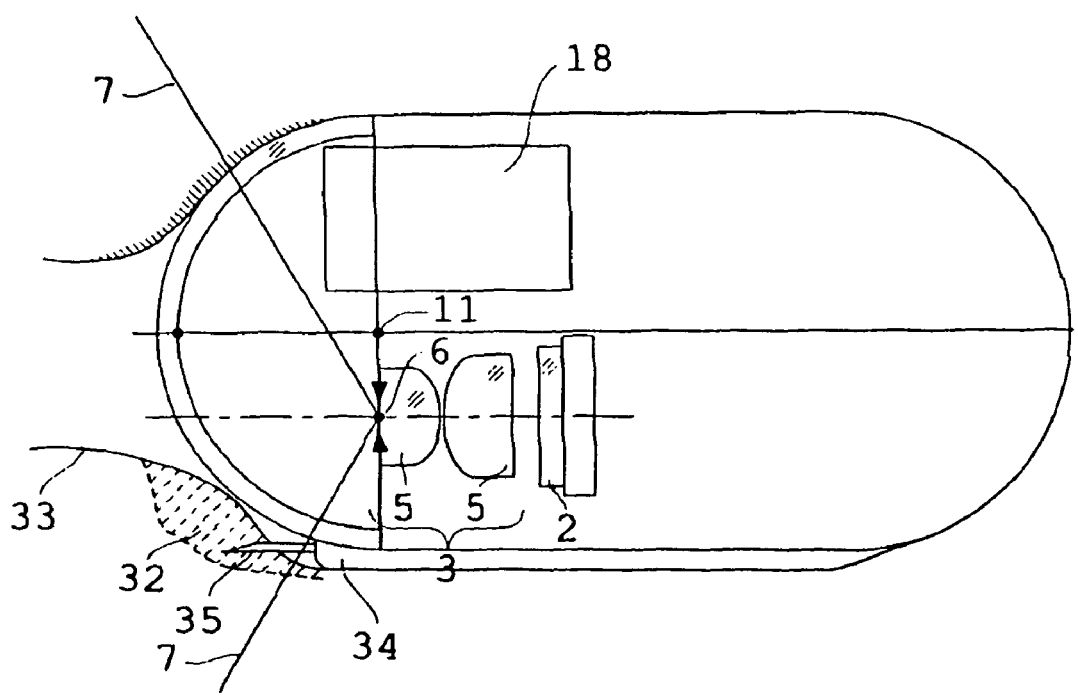
FIG. 8 shows an exemplary structure of a capsule-type endoscope that is provided with a delivery tube having a puncture needle at one end of the delivery tube.

FIG. 8 shows an exemplary structure of a capsule-type endoscope that is provided with a solution delivery tube having a puncture needle at one end of the solution delivery tube. In the capsule-type endoscope in FIG. 8, a projection port 34 for the puncture needle is provided at a position that is outside the outer limits 7 of the field of view of the objective optical system 3, but the tip of the puncture needle 35 is inside the field of view so that the insertion position of the puncture needle may be observed before the puncture needle is actually inserted into the living tissue. The puncture needle projection port 34 is designed to expand the inner wall 33 of a tubular organ, and thereby create an empty space between the puncture needle projection port 34 and the observation target region 32 that is within the field of view of the objective optical system.

With such a structure, the positional relationship between the puncture needle 35 and the observation target region 32 of the living tissue may be determined before the tip of the puncture needle 35 is inserted into the observation target region 32. Therefore, the puncture needle tip may be prevented from puncturing the living tissue at an unintended point, and the puncture needle tip may be prevented from extending entirely through the living tissue. The puncture needle 35 may be stored inside the capsule and pushed out of the projection port 34 by a mechanism when the capsule-type endoscope approaches the observation target region 32 within the outer limits 7 of the field of view. Moreover, the puncture needle 35 is provided with markings, which may be in different colors, at regular intervals from its tip that may be observed via a monitor to determine the depth that the tip of the puncture needle 35 has been inserted into the observation target region 32.

Figure 23A:
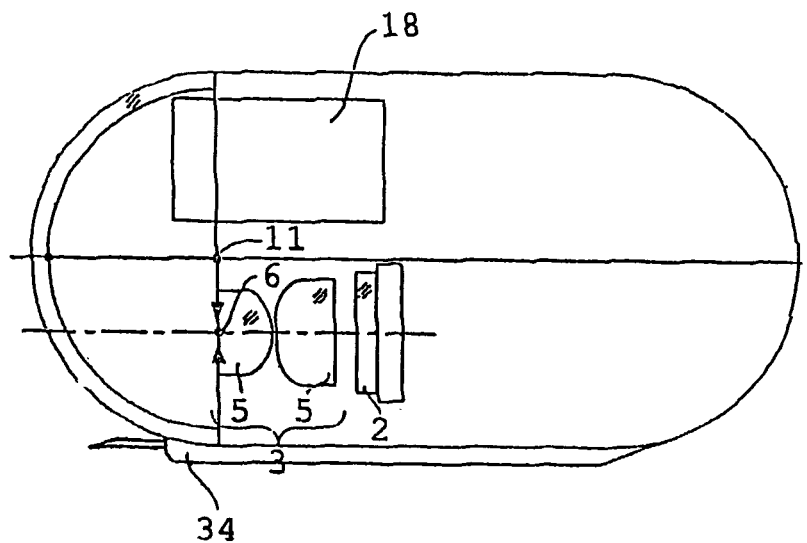
FIGS. 23(a) and 23(b) show a capsule-type endoscope in which a puncture needle projection port, a puncture needle storage part, and a mechanism for pushing out the puncture needle are constituted as a unit that is detachably attached to the capsule-type endoscope.
Figure 23B:
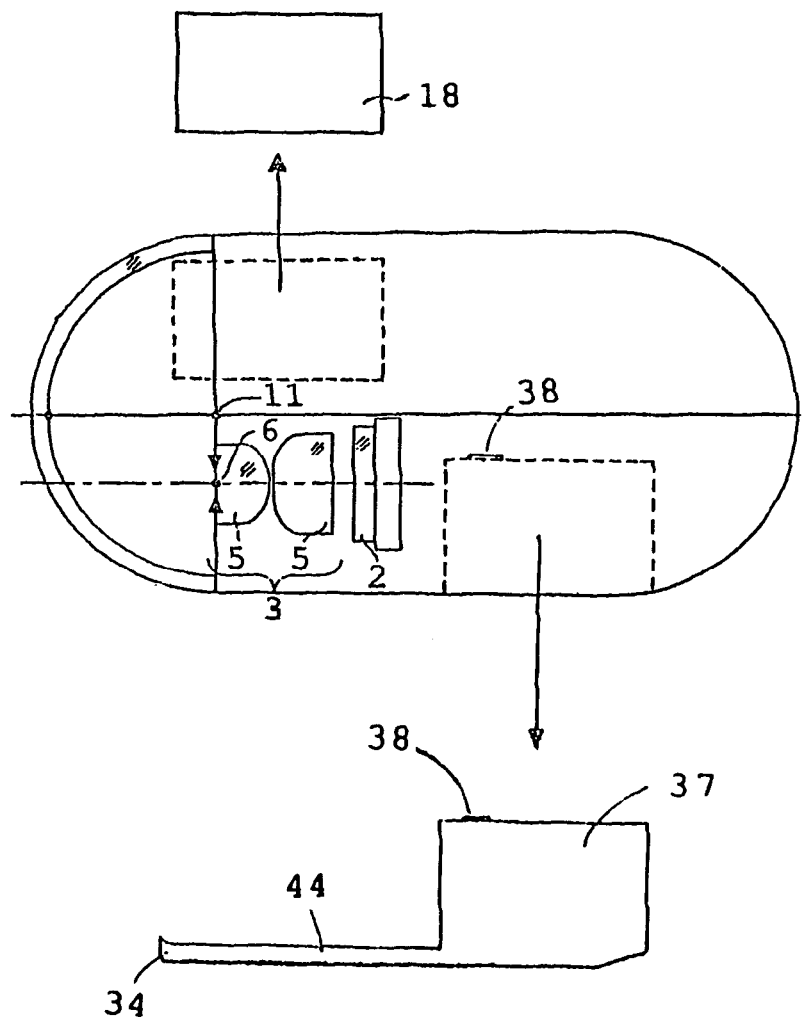

As shown in FIGS. 23(a) and 23(b), the projection port 34 of the puncture needle, a puncture needle storage part 44, and a mechanism 37 for pushing out the puncture needle may be formed as a unit that may be detachably attached to the capsule-type endoscope. In such a case, it is preferred that an electrical connection 38 be provided at the joint between the capsule and the detachable unit so that power is supplied from the capsule to the mechanism 37 for pushing out the puncture needle.

Figure 9:
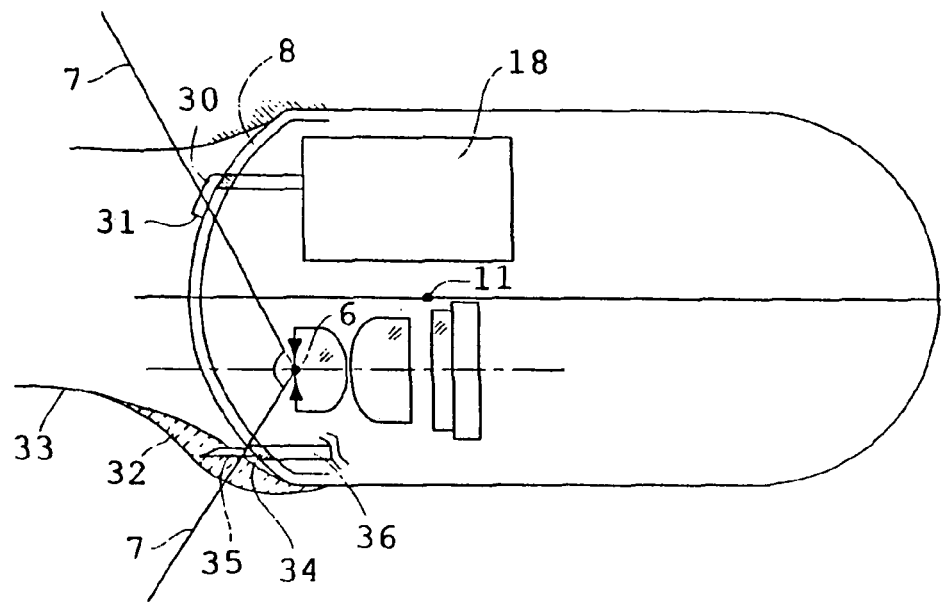
FIG. 9 shows another exemplary structure of a nozzle, as well as of a puncture needle projection port, with the capsule being shown in cross-section as viewed from the side.

FIG. 9 is an illustration to show another exemplary structure of a nozzle 30, as well as of a puncture needle projection port 34. In this structure, the nozzle 30 and the puncture needle projection port 34 project through the transparent cover 8. The nozzle 30 is connected to the tank 18 through the transparent cover 8 at a position that is outside the outer limits 7, 7 of the field of view of the objective optical system. A jet orifice 31 is provided within the outer limits 7, 7 of the field of view of the objective optical system. The puncture needle projection port 34 is positioned so that the puncture needle protrudes through the transparent cover 8 at a point that is outside the outer limits 7, 7 of the field of view of the objective optical system. A delivery tube 36 that is connected to the puncture needle 35 may be connected to another tank (not shown). The front surface of the transparent cover 8 is designed so that a space exists between the puncture needle projection port 34 and the observation target region 32 of the living tissue. This enables the positional relationship between the puncture needle 35 and the living tissue to be observed. It is desired that the positional relationship between the image pickup unit and the inner surface of the transparent cover 8 satisfy Condition (1) above, but this is not required.

Figure 10:
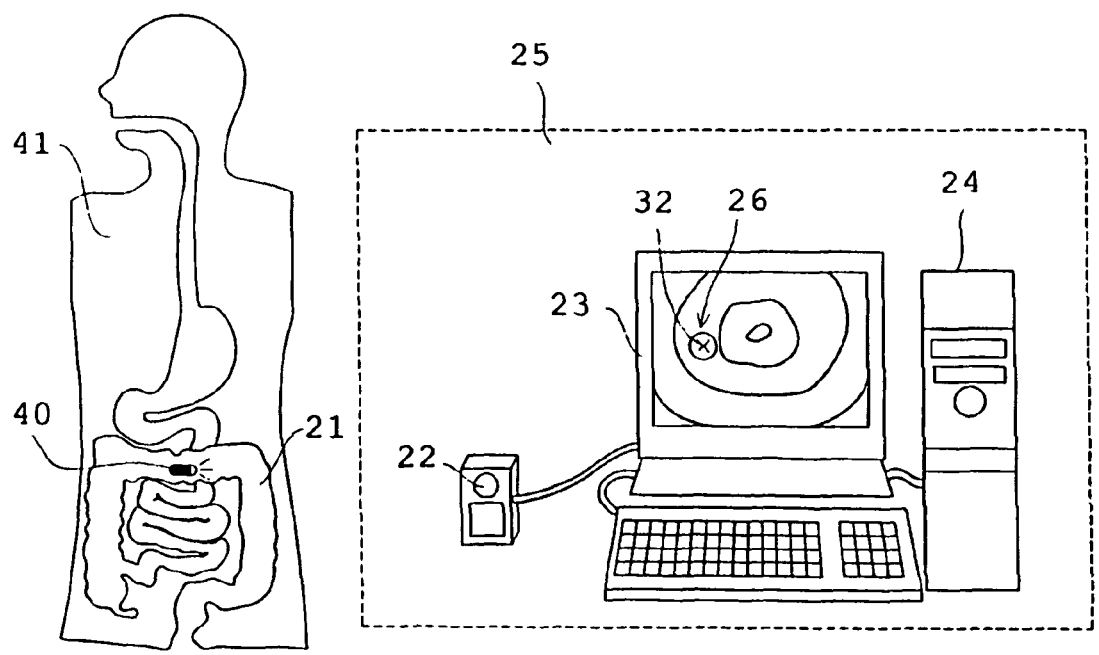
FIG. 10 is an illustration to explain the capsule-type endoscope system of the present invention that may be used to observe the inner wall of a person's digestive tract.

FIG. 10 is an illustration to explain the operation of a capsule-type endoscope system for observing the inner wall of the digestive tract. In FIG. 10, the equipment enclosed by the dotted lines is an image display system 25 that is provided externally of the patient. A patient 41 is dressed in specifically designed clothing for externally controlling the orientation of the capsule-type endoscope 40 moving within the digestive tract 21. For example, electromagnetic induction units, not shown in the figure, may be used for this purpose. Image signals that are wirelessly transmitted from a communication unit that is positioned within the capsule-type endoscope 40 are received by a communication device 22 that is provided externally of the patient. The communication device 22 may be connected to a personal computer 24 for processing the image signals. The images that are processed by the personal computer 24 may be displayed on a monitor 23. The personal computer 24 is also provided with a memory device for storing the image signals. For example, a target symbol 26 can be marked at a point ("x" in the figure) where the centerline of the jet orifice 31 intersects an object to be viewed (i.e., the inner wall of the digestive tract 21). In this manner, one can ensure that a substance in liquid form is accurately sprayed onto an observation target region 32 (such as a possible lesion) within the field of view of the objective optical system.

During an observation while the capsule-type endoscope 40 proceeds along within the digestive tract 21, the observation target region 32 is captured by the image pickup unit between the far point and the mid point of the depth of field of the objective optical system. The orientation of the capsule-type endoscope 40 may be controlled so that the target symbol 26 overlaps the observation target region 32. A series of operations, including the display of the target symbol 26, the orientation control of the capsule-type endoscope 40, and the spraying of a substance in liquid form can be executed using one or more of a keyboard, a mouse, and a joy stick that are connected to the personal computer 24.

The personal computer 24 may be used for tracking and controlling the capsule-type endoscope. For example, the personal computer 24 may function to automatically control a series of operations, such as automatic tracking of the capsule-type endoscope and the delivery of a substance that is sprayed onto an intended target region. With the personal computer 24 providing such a function, an observer may view images from the capsule-type endoscope that are displayed on the monitor 23 and may move a cursor over the observation target region 32 so as to specify automatic tracking of a target and the commencement of an automatic spray function. Alternatively, the personal computer 24 may provide the function of analyzing the morphology and color tone of an object captured by the image pickup unit. Screening for particular lesion patterns stored in the memory of the personal computer 24 may be performed concurrently with image processing and automatic target tracking. A substance in liquid form (such as a coloring agent or a drug) may be sprayed from the jet orifice 31 when the observation target region 32 and the target symbol 26 overlap on the monitor 23 in the course of automatic tracking. When automatically determining a tracking target by analyzing the morphology and color tone of the images captured by the image pickup unit, an indication to draw the observer's attention may be displayed on the monitor 23 when a lesion that may become a tracking target is first identified.

Should an observer determine by observing the received images that there is no need for spraying, the observer can cancel the automatic tracking operation by, for example, using a keyboard that is connected to the personal computer 24. When using a capsule-type endoscope that is provided with a delivery tube and a puncture needle, the personal computer 24 may be provided with an image processing function so as to determine from captured images the depth that a puncture needle has been inserted into a living tissue after it first contacts the surface of a living tissue and so as to display the result on a monitor. Furthermore, a marking 39 (such as an "x") can be displayed at a position where the tip of the puncture needle will make contact with the living tissue surface, based on the positional relationship between the puncture needle projection port 34, the position of the observation target region 32 of the living tissue and the moving direction of the puncture needle.

As shown by the diagonal, broken lines in the region 32' of FIG. 6, the observation target region 32 that is sprayed with a substance gradually approaches the objective optical system 3 and makes contact with the outer surface 9 of the transparent cover 8 near the near point of the depth of field of the objective optical system 3. Therefore, it is desired that the image pickup unit 1, which includes the objective optical system 3 and the image pickup element 2, has its highest resolution for objects near the outer surface 9 of the transparent cover 8 so that the region 32' can be viewed very clearly and a diagnosis made of the region 32'. In other words, it is desired for the structure in FIG. 6 to satisfy the following Conditions (2) and (3):

$$R1 \geq 5 \text{ lines per mm} \qquad \text{Condition (2)}$$

$$R2 \geq 1 \text{ line per mm} \qquad \text{Condition (3)}$$

where

R1 is the resolution on the optical axis at positions between the most object-side surface of the objective optical system and the point of intersection of the optical axis of the objective optical system with the outer surface of the transparent cover; and R2 is the resolution, as will be defined below, on the optical axis at positions between the most object-side surface of the objective optical system and the far point of the depth of field of the objective optical system.

The term "resolution" (as will be defined below) is measured as follows. Pairs of black and white lines are captured by the image pickup unit and displayed on a monitor via a system for processing image signals transmitted from the solid-state image pickup element. The contrast I of the black/white line pairs on the monitor is obtained using the following Equation (A):

$$I = (I\max - I\min)/(I\max + I\min) \qquad \text{Equation (A)}$$

where

Imax and Imin are the maximum and minimum values of the black and white intensity profile, respectively.

'Resolution' is defined as the reciprocal of the width (in mm) of the black/white line pair when the contrast I, as set forth above, is 10%. Thus, "a resolution of 5 lines/mm or higher" means that the contrast of black/white line pairs having a width of 0.2 mm is 10% or more on the monitor. Similarly, a resolution of 1 line/mm or higher means that the contrast of black/white line pairs having a width of 0.5 mm is 10% or more on the monitor. When the image pickup unit 1 has a resolution of 5 lines/mm or higher for an object point distance A1, the living tissue near the outer surface of the transparent cover can be enlarged on the monitor 23 for observation. Particularly, it is important for a capsule-type endoscope to allow for close-up observation of villi, which are small projections that extend from the wall of the small intestine. Villi are approximately 0.2 to 0.5 mm in width; therefore a resolution higher than this is required for good observation. When the image pickup unit 1 has a resolution of 1 line/mm or higher for an object point distance B1, the observation target region 32 can be easily found at the far point of the field of view when displayed on the monitor 23.

It is desired that the image pickup unit 1 is provided with an image pickup element 2 and objective optical system 3 that satisfies the following Conditions (4)-(6):

$$80 < IH/P < 500 \qquad \text{Condition (4)}$$

$$80 < FL/P < 500 \qquad \text{Condition (5)}$$

$$400 < Fno/P < 3000 \qquad \text{Condition (6)}$$

where

IH is the distance (in mm) between the center and the point most distant from the center of the effective image pickup area of the light-receiving surface of the image pickup element;

P is the horizontal pixel pitch (in mm) of the image pickup element;

FL is the focal length (in mm) of the objective optical system; and

Fno is the effective F-number of the objective optical system.

When the value of IH/P equals or exceeds 500 (i.e., does not satisfy the upper limit of Condition (4)), a larger depth of field cannot be obtained when used in combination with the objective optical system. On the other hand, when the value of IH/P does not satisfy the lower limit of Condition (4), a required resolution cannot be obtained near the near point of the depth of field.

When the value of FL/P equals or exceeds 500 (i.e., does not satisfy the upper limit of Condition (5)), the depth of field will become small when used in combination with the objective optical system. On the other hand, when the value of FL/P does not satisfy the lower limit of Condition (5), it is difficult to obtain a desired resolution at the object point distance A1.

When the value of Fno/P equals or exceeds 3000 (i.e., does not satisfy the upper limit of Condition (6)), the required resolution will exceed the optical diffraction limit, and thus high quality images will be unattainable even though the images are in focus. When the value of Fno/P is 400 or less (i.e., does not satisfy the lower limit of Condition (6)), the depth of field will become small; a desired resolution will be obtained at the object point distance A1 while focal shifts will occur at the object point distance B1.

For example, it is preferred for a capsule-type endoscope having an outer diameter of approximately 10 mm to have an object point distance A1 of 3 mm and an object point distance B1 of 50 mm. The objective optical system 3 consists of two positive lens elements in the disclosed embodiments of the present invention. However, the objective optical system 3 of the capsule-type endoscope of the present invention is not restricted to such a lens structure.

Embodiment 2 and Three Possible Modifications

Figures 11A, 11B:
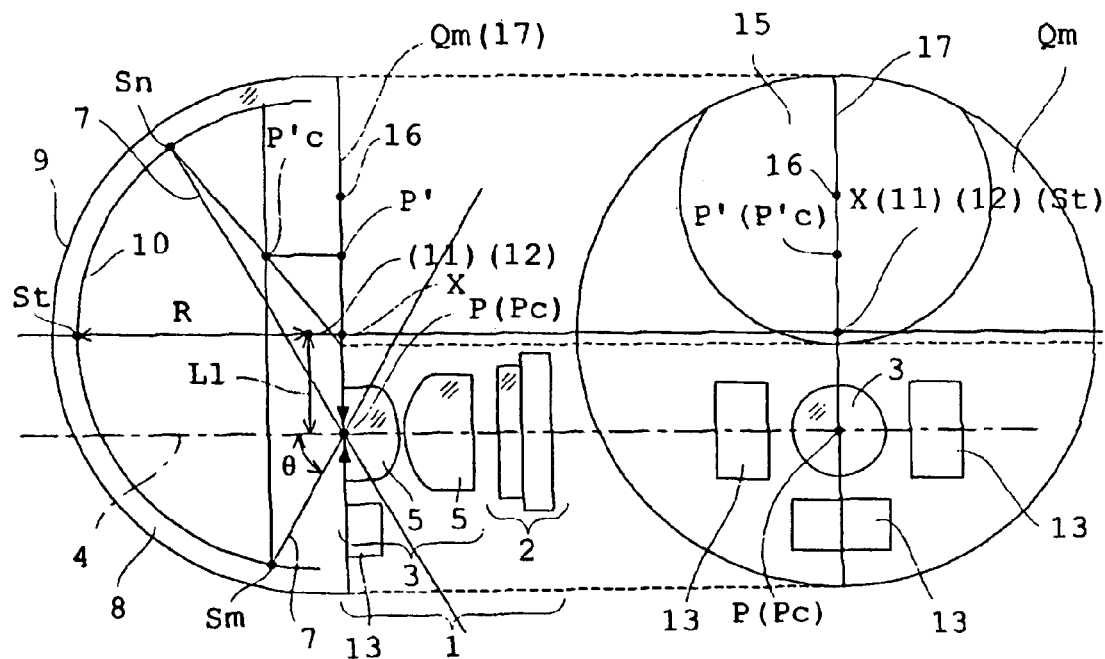
FIGS. 11(a) and 11(b) illustrate Embodiment 2 of the present invention, with FIG. 11(a) being a cross-section of a front portion of the capsule-type endoscope as viewed from the side, and FIG. 11(b) being a cross-section of a front portion of the capsule-type endoscope as viewed from the front.

FIGS. 11(a)-14(b) are illustrations of cross-sections of the front portion of the capsule-type endoscope according to Embodiment 2, and three possible modifications to Embodiment 2, of the present invention. FIG. 11(a) is a cross-section of a front portion of the capsule-type endoscope of Embodiment 2 as viewed from the side, and FIG. 11(b) is a cross-section of a front portion of the capsule-type endoscope of Embodiment 2 as viewed from the front.

In the capsule-type endoscope of Embodiment 2 shown in FIGS. 11(a) and 11(b), the inner surface 10 of the transparent cover 8 is spherical. The center of curvature 11 of the inner surface 10 of the transparent cover 8 is on the object side of a line 17 that passes through the center Pc of the entrance pupil of the objective optical system 3 and is orthogonal to the optical axis 4 of the objective optical system 3. The objective optical system 3 is provided in such a manner that the entrance pupil thereof is in the same plane as a plane Qm that contains the light emitting surface(s) 14 (see FIG. 12(a)) of the illumination light source(s) that form the illumination means 13.

Furthermore, in the capsule-type endoscope of Embodiment 2 shown in FIGS. 11(a) and 11(b), the objective optical system 3 is positioned so that the point of intersection X with the plane Qm of a line drawn from the vertex St of the inner surface 10 of the transparent cover so as to be perpendicular to the plane Qm lies on the longitudinal axis of the capsule, and the point X is on a line that connects the intersection points P and P'. Points that happen to be coincident in the figures are labeled with multiple labels, with the second label listed in parenthesis. P is the intersection with a plane Qm of a line drawn from the center Pc of the entrance pupil of the objective optical system 3 so as to be perpendicular to the plane Qm. Thus, in FIG. 11(a), P and Pc are coincident and the position thereof is labeled P(Pc). P' is the intersection with the plane Qm of a line drawn from the intersection point P'c so as to be perpendicular to the plane Qm. P'c is the intersection point of hypothetical light rays that emerge from the center Pc of the entrance pupil of the objective optical system 3 and are reflected by the inner surface 10 of the transparent cover 8 at the points Sm and Sn that define the outer limits of the field of view of the objective optical system 3 in the plane (depicted in FIG. 11(a)) that contains the vertex St of the inner surface of the transparent cover and the optical axis of the objective optical system. In this embodiment, three illumination light sources of the illumination means 13 are provided outside the reflected image range 15 of the entrance pupil of the objective optical system 3 when the image of the entrance pupil is projected via the inner surface 10 of the transparent cover 8 back onto the plane Qm.

Figures 12A, 12B:
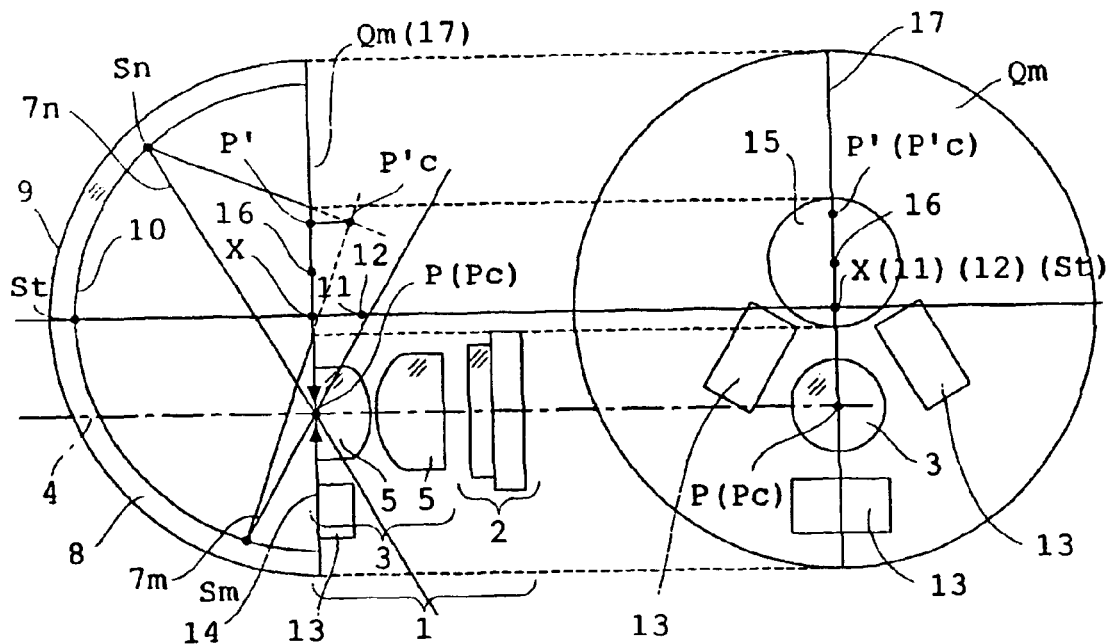
FIGS. 12(a) and 12(b) illustrate a first possible modification to Embodiment 2 of the present invention, with FIG. 12(a) being a cross-section of a front portion of the capsule-type endoscope as viewed from the side, and FIG. 12(b) being a cross-section of a front portion of the capsule-type endoscope as viewed from the front.

FIGS. 12(a) and 12(b) show a first possible modification to Embodiment 2, with FIG. 12(a) being a cross-section of a front portion of the capsule-type endoscope according to the first possible modification of Embodiment 2 as viewed from the side, and FIG. 12(b) being a cross-section of a front portion of the capsule-type endoscope according to the first possible modification of Embodiment 2 as viewed from the front. In this capsule-type endoscope, the inner surface 10 of the transparent cover 8 is spherical. The center of curvature 11 of the inner surface 10 of the transparent cover 8 is on the image side of a line 17 that passes through the center Pc of the entrance pupil of the objective optical system 3 and is orthogonal to the optical axis 4 of the objective optical system 3. The objective optical system 3 is positioned so that the entrance pupil plane thereof lies in the same plane as the plane Qm that contains the light emitting surfaces 14 of the illumination light sources that form the illumination means 13.

Furthermore, in the possible modification to Embodiment 2 shown in FIGS. 12(a) and 12(b), the objective optical system 3 is positioned such that the intersection X with the plane Qm of a line drawn from the vertex St of the inner surface 10 of the transparent cover perpendicular to the plane Qm is on a line that connects the points P and P', where Qm, P and P' are as previously defined. In the possible modification shown in FIGS. 12(a) and 12(b), three illumination light sources form the illumination means 13 and these illumination light sources are provided outside the reflected image range 15 of the entrance pupil of the objective optical system 3.

In the capsule-type endoscope of the present invention according to Embodiment 2 shown in FIGS. 11(a) and 11(b), and the first possible modification shown in FIGS. 12(a) and 12(b), four areas are defined by the lines 7m and 7n that lie within a plane that contains the optical axis 4 of the objective optical system 3 and the vertex St of the inner surface 10 of the transparent cover 8. The lines 7m and 7n are drawn through the center of the entrance pupil of the objective optical system 3 so as to pass through the points Sm and Sn on the inner surface 10 of the transparent cover 8 that define the outer limits of the field of view of the objective optical system in the cross-section (depicted in FIG. 12(a)) that contains the vertex St of the inner surface of the transparent cover and the center Pc of the entrance pupil of the objective optical system. As is apparent from FIG. 12(b), the center of curvature 11 of the portion of the inner surface 10 of the transparent cover 8 that is within the field of view of the objective optical system 3 is in a sector (among the four sectors delineated by the intersection of lines 7m and 7n when these lines are extended backward as shown in FIG. 12(a)) that does not include the optical axis of the objective optical system 3. In the capsule-type endoscope of Embodiment 2 and the first possible modification as discussed above, the center of curvature 11 of the inner surface 10 of the transparent cover 8 coincides with the center of curvature of the portion of the inner surface 10 of the transparent cover 8 that is within the field of view of the objective optical system 3. Among the four sectors delineated by the intersection of the lines 7m and 7n when these lines are extended backward as shown in FIG. 12(a), when the center of curvature 11 of the inner surface 10 of the transparent cover 8 lies within a sector that includes the optical axis 4 of the objective optical system 3, the reflected image range 15 (defined above) of the entrance pupil of the objective optical system 3 will be larger than desired and thus will not leave a sufficient space for providing the illumination light source(s) that form the illumination means 13.

Figures 15A, 15B:
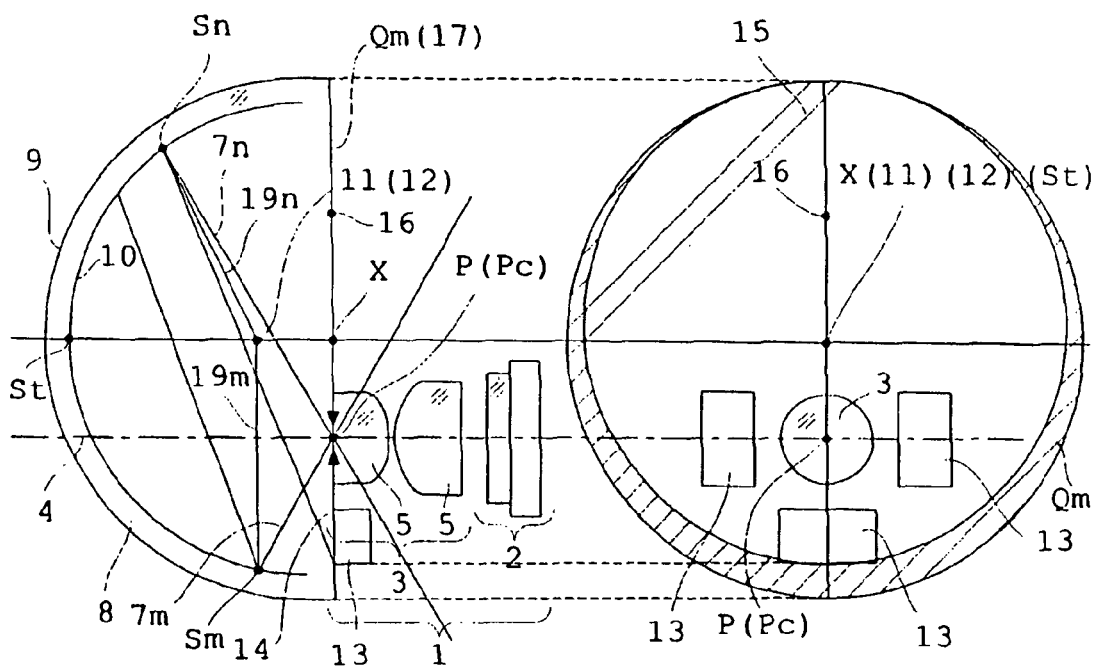
FIGS. 15(a) and 15(b) are illustrations to show exemplary structure of a capsule-type endoscope according to the present invention so as to clarify the differences between the present invention versus prior art capsule-type endoscopes, with FIG. 15(a) being a cross-section of a front portion of a capsule-type endoscope according to the present invention as viewed from the side, and FIG. 15(b) being a cross-section of a front portion of a capsule-type endoscope according to the present invention as viewed from the front.

This issue will now be discussed with reference to FIGS. 15(a) to 16(b). FIGS. 15(a) and 15(b) are illustrations to show exemplary structure of a capsule-type endoscope according to the present invention so as to clarify the differences between the present invention versus prior art capsule-type endoscopes, with FIG. 15(a) being a cross-section of a front portion of the capsule-type endoscope as viewed from the side, and FIG. 15(b) being a cross-section of a front portion of the capsule-type endoscope as viewed from the front.

In the capsule-type endoscope shown in FIGS. 15(a) and 15(b), the center of curvature 11 of the inner surface 10 of the transparent cover 8 is in a sector (among the four sectors delineated by the intersection of the lines 7m and 7n when these lines are extended backward as shown in FIG. 15(a)) that contains the optical axis of the objective optical system 3 and is on the object side of the center Pc of the entrance pupil of the objective optical system 3. As before, the lines 7n and 7m are drawn from the center of the entrance pupil of the objective optical system to the points Sn and Sm that define the outer limits of the field of view of the objective optical system cross-section (depicted in FIG. 15(a)) that contains the vertex St of the inner surface of the transparent cover and the center Pc of the entrance pupil of the objective optical system. Therefore, the line 7m is on the image side (i.e., is to the right in FIG. 15(a)) of the line 19m that connects the center of curvature 11 to the outer boundary point Sm, and the line 7n is on the image side of the line 19n that connects the center of curvature 11 to the outer boundary point Sn (Sm and Sn are as defined previously). Once again it is assumed that hypothetical light rays come from the center Pc of the entrance pupil of the objective optical system 3 and are reflected at the outer boundary points Sm and Sn of the field of view in the plane of FIG. 15(a). The light reflected at the point Sm proceeds toward the object side (i.e., to the left in FIG. 15(a)) of the line 19m that connects the center of curvature 11 to the outer boundary point Sm. The light reflected at the outer boundary point Sn also proceeds toward the object side of the line 19n that connects the center of curvature 11 to the outer boundary point Sn of the field of view in the plane of FIG. 15(a). When the hypothetical light rays that come from the center Pc of the entrance pupil of the objective optical system 3 are reflected at the outer boundary points Sm and Sn, the reflected image range 15 of the entrance pupil of the objective optical system 3 (as defined previously) will become excessively large.

FIG. 15(b) illustrates the reflected image range 15 (as defined above) of the entrance pupil of the objective optical system 3 onto the plane Qm that contains the light emitting surface(s) of the light source(s) that form the illumination means 13.

Figures 16A, 16B:
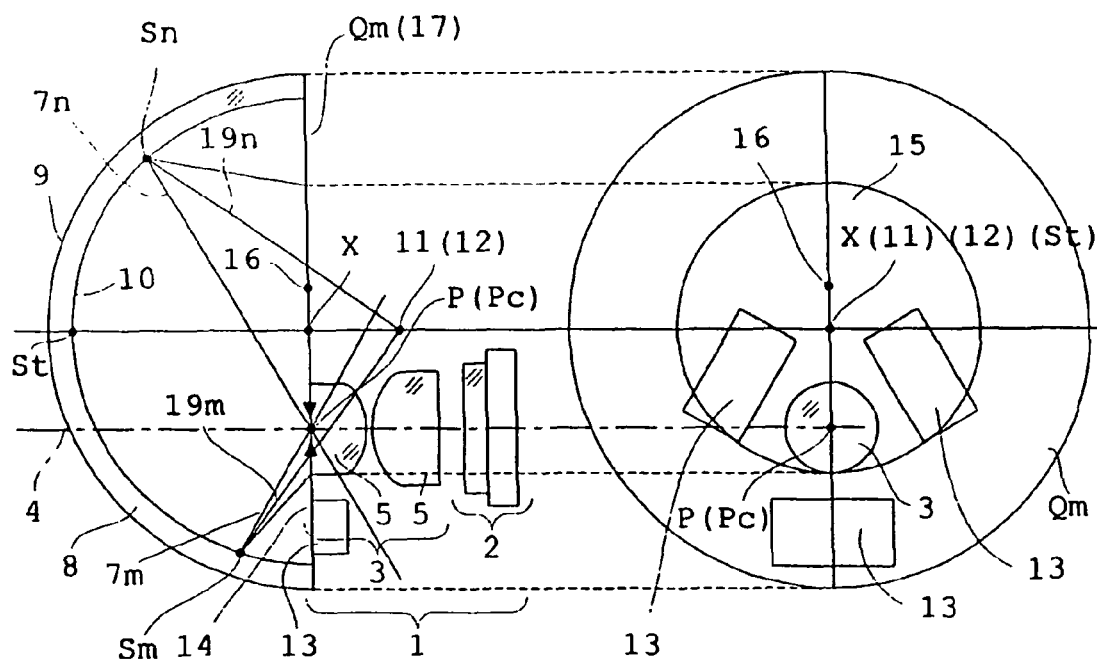
FIGS. 16(a) and 16(b) show another exemplary structure of a capsule-type endoscope according to the present invention so as to clarify the differences between the present invention versus prior art capsule-type endoscopes, with FIG. 16(a) being a cross-section of a front portion of a capsule-type endoscope according to the present invention as viewed from the side, and FIG. 16(b) being a cross-section of a front portion of a capsule-type endoscope according to the present invention as viewed from the front.

FIGS. 16(a) and 16(b) show another exemplary structure of a capsule-type endoscope according to the present invention so as to clarify the differences between the present invention versus prior art capsule-type endoscopes, with FIG. 16(a) being a cross-section of a front portion of the capsule-type endoscope as viewed from the side, and FIG. 16(b) being a cross-section of a front portion of the capsule-type endoscope as viewed from the front. In FIGS. 16(a) and 16(b), the center of curvature 11 of the inner surface 10 of the transparent cover 8 is in a sector (among the four sectors delineated by the intersection of the lines 7m and 7n when these lines are extended backward as shown in FIG. 16(b)) that contains the optical axis of the objective optical system and is on the image side of the center Pc of the entrance pupil of the objective optical system 3. Therefore, the line 7m is on the object side (i.e., is to the left in FIG. 16(a)) of the line 19m that connects the center of curvature 11 to the outer boundary point Sm, and the line 7n is also on the object side of the line 19n that connects the center of curvature 11 to the outer boundary point Sn, where both Sm and Sn are as defined previously. It is assumed that hypothetical light rays come from the center Pc of the entrance pupil of the objective optical system 3 and are reflected at the outer boundary points Sm and Sn of the field of view in the cross-section (depicted in FIG. 16(a)) that contains the vertex St of the inner surface of the transparent cover and the center Pc of the entrance pupil of the objective optical system. The light reflected at the point Sm proceeds toward the image side (i.e., to the right in FIG. 16(a)) of the line 19m that connects the center of curvature 11 to the outer boundary point Sm. The light reflected at the outer boundary point Sn also proceeds toward the image side of the line 19n that connects the center of curvature 11 to the outer boundary point Sn of the field of view in the plane of the figure. When the hypothetical light rays that come from the center Pc of the entrance pupil of the objective optical system 3 are reflected at the outer boundary points Sm and Sn, the reflected image range 15 of the entrance pupil of the objective optical system 3 will become excessively large on the plane Qm that contains the light-emitting surface(s) of the light source(s) that form the illumination means 13 and will overlap with the objective optical system 3, as shown in FIG. 16(b).

As described above, it is preferred, for a capsule-type endoscope embodiment in which the inner surface 10 of the transparent cover is spherical, that the center of curvature 11 of the inner surface 10 of the transparent cover 8 is in a sector (among the four sectors defined by the lines 7m and 7n when these lines are extended backward as shown in FIG. 16(b)) that does not contain the optical axis of the objective optical system.

It is further preferred that the center of curvature 11 of the inner surface 10 of the transparent cover 8 and the center Pc of the entrance pupil of the objective optical system 3 are positioned so as to satisfy the above Condition (1).

When the upper limit of Condition (1) is not satisfied, the objective optical system 3 will be too close to the vertex St of the inner surface 10 of the transparent cover 8 and not leave a sufficient space to accommodate the illumination light source (s) of the illumination means 13. When the lower limit of the Condition (1) is not satisfied, the objective optical system 3 will be too far away from the vertex St of the inner surface 10 of the transparent cover 8, thereby increasing the entire capsule length.

Figures 13A, 13B:
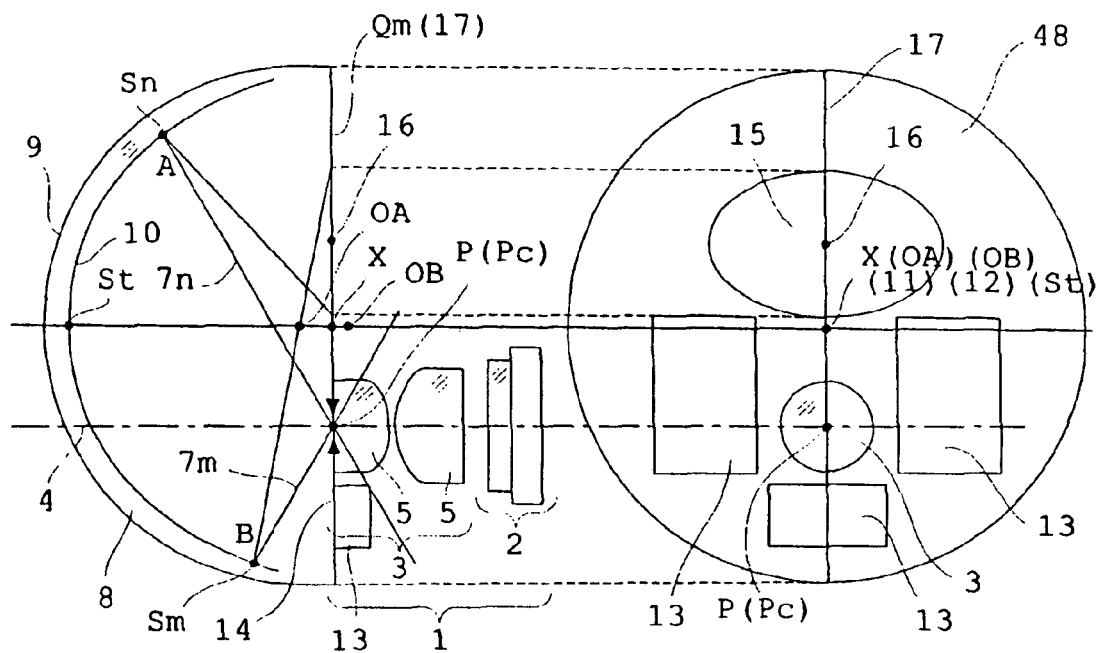
FIGS. 13(a) and 13(b) illustrate a second possible modification to Embodiment 2 of the present invention, with FIG. 13(a) being a cross-section of a front portion of the capsule-type endoscope as viewed from the side, and FIG. 13(b) being a cross-section of a front portion of the capsule-type endoscope as viewed from the front.
Figures 14A, 14B:
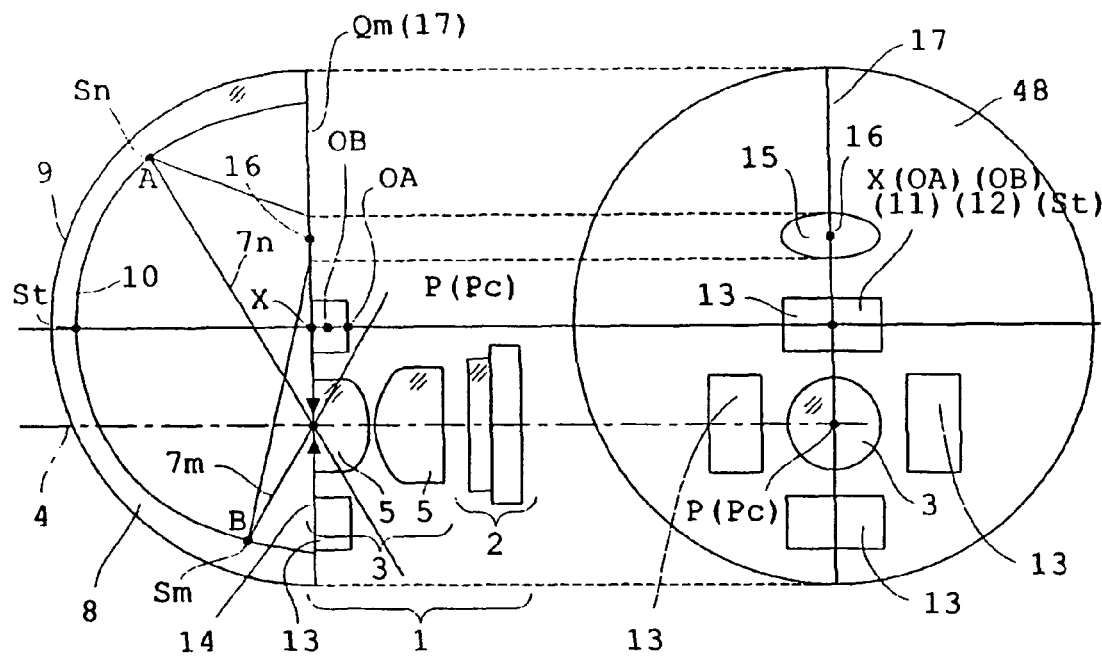
FIGS. 14(a) and 14(b) illustrate a third possible modification to Embodiment 2 of the present invention, with FIG. 14(a) being a cross-section of a front portion of the capsule-type endoscope as viewed from the side, and FIG. 14(b) being a cross-section of a front portion of the capsule-type endoscope as viewed from the front.

FIGS. 13(a) and 13(b) and FIGS. 14(a) and 14(b) show second and third possible modifications to Embodiment 2, with FIGS. 13(a) and 14(a) being cross sections as viewed from the side, with the plane of the cross-section including the optical axis of the objective optical system and the vertex St of the inner surface of the transparent cover, and FIGS. 13(b) and 14(b) being cross sections as viewed from the front. In the second possible modification shown in FIGS. 13(a) and 13(b), the inner surface 10 of the transparent cover 8 is an aspheric surface wherein the curvature increases with increasing distance from the vertex St of the inner surface. In the third possible modification shown in FIGS. 14(a) and 14(b), the inner surface 10 of the transparent cover 8 is an aspheric surface wherein the curvature decreases with increasing distance from the vertex St of the inner surface. When the inner surface 10 of the transparent cover 8 is aspheric, the transparent cover 8 and the objective optical system 3 are positioned as follows: the curvature (curvature is defined as 1 divided by the radius of curvature R at the point of interest) at the points Sm and Sn (both as defined previously) is obtained and the centers of curvature OA and OB of spherical surfaces having a curvature of 1/R are positioned in a sector (among the four sectors delineated by the lines 7m and 7n when these lines are extended backward as shown in FIGS. 13(a) and 14(a)) that does not contain the optical axis of the objective optical system.

In the second and third possible modifications to the capsule-type endoscope of Embodiment 2 that are shown in FIGS. 13(a) to 14(b), the objective optical system 3 is positioned so that the point of intersection X with the plane Qm of a line drawn from the vertex St perpendicular to the plane Qm (St and Qm are as defined previously) is on a line that connects the point P and the center 16 of the reflected image range 15. In these possible modifications, multiple illumination light sources are provided and are positioned outside the reflected image range 15. With the second and third possible modifications to Embodiment 2 shown in FIGS. 13(a) to 14(b), a sufficient space for providing the image pickup unit 1 while using multiple illumination light sources is ensured even if the inner surface 10 of the transparent cover 8 is aspheric. Therefore, a small-sized, capsule-type endoscope can be provided that prevents illumination light that is reflected by the inner surface 10 of the transparent cover 8 from causing flare in the objective optical system 3.

Embodiment 3

Figure 17:
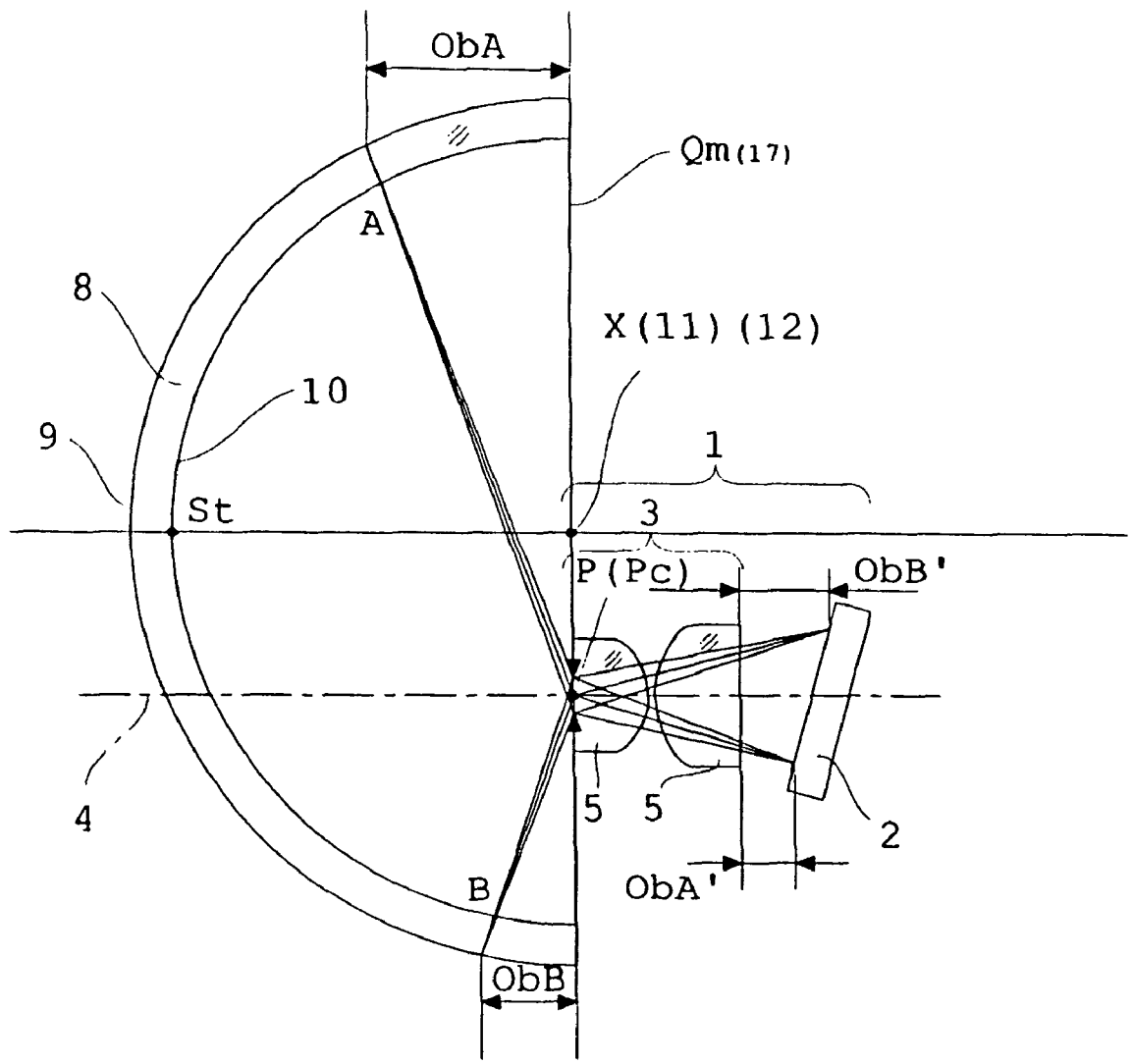
FIG. 17 relates to Embodiment 3 of the present invention, and illustrates the imaging of object points that are on the outer surface of the transparent cover at the outer limits of the field of view of the objective optical system.

FIG. 17 shows a cross-section of a front portion of a capsule-type endoscope according to Embodiment 3 of the present invention, as viewed from the side. More specifically, it illustrates 10 a cross section that contains the optical axis 4 of the objective optical system 3 and the vertex St of the inner surface 10 of the transparent cover 8, and shows the imaging of an object point that is positioned on the outer surface 9 of the transparent cover 8 at the outer limits of the field of view of the objective optical system 3. The image pickup unit I of the capsule-type endoscope of Embodiment 3 includes an objective optical system 3 having lens components 5, 5 (which may each consist of a single lens element), a diaphragm (not shown), a lens frame (not shown), a spacer ring (not shown), an image pickup element 2, and an image pickup element frame (not shown).

As shown in FIG. 17, the center of the field of view of the objective optical system 3 is positioned off the longitudinal axis of the capsule; thus, the distance between the most object-side surface of the objective optical system 3 and the outer surface 9 of the transparent cover 8 varies, depending on the viewing direction. This causes the image position for each object point to shift. Therefore, if the image pickup surface of the image pickup element 2 is positioned orthogonal to the optical axis as in prior art capsule-type endoscopes, objects that are in contact with the outer surface of the transparent cover 8 at the outer limits of the field of view of the objective optical system 3 will be partially out of focus, making observations difficult.

Hence, in the endoscope of Embodiment 3 (as shown in FIG. 17), the image pickup element 2 is tilted so as to be non-orthogonal to the optical axis of the objective optical system 3 in such a manner that the image pickup surface is positioned at the image positions ObA' and ObB', which correspond to the distances ObA and ObB between the most object-side surface of the objective optical system 3 and the outer surface 9 of the transparent cover 8 at the outer limits of the field of view of the objective optical system 3. With a capsule-type endoscope having such a structure, focal shifts on the image plane caused by differences in object point distances to the outer surface 9 of the transparent cover 8 in different viewing directions can be corrected, and a small-sized, capsule-type endoscope that allows for clear observation of objects that are in contact with the outer surface 9 of the transparent cover 8 can be realized.

When it is difficult to tilt the image pickup element 2 in a manner such that the image-forming points at the image positions ObA and ObB completely coincide with the image pickup surface, the tilt of the image pickup element 2 can be adjusted relative to the optical axis of the objective optical system 3 in such a manner that the diameter of a light flux on the image pickup surface extends over approximately four pixels for any viewing direction, as this yields images that are practically in focus.

Embodiment 4

Figure 18:
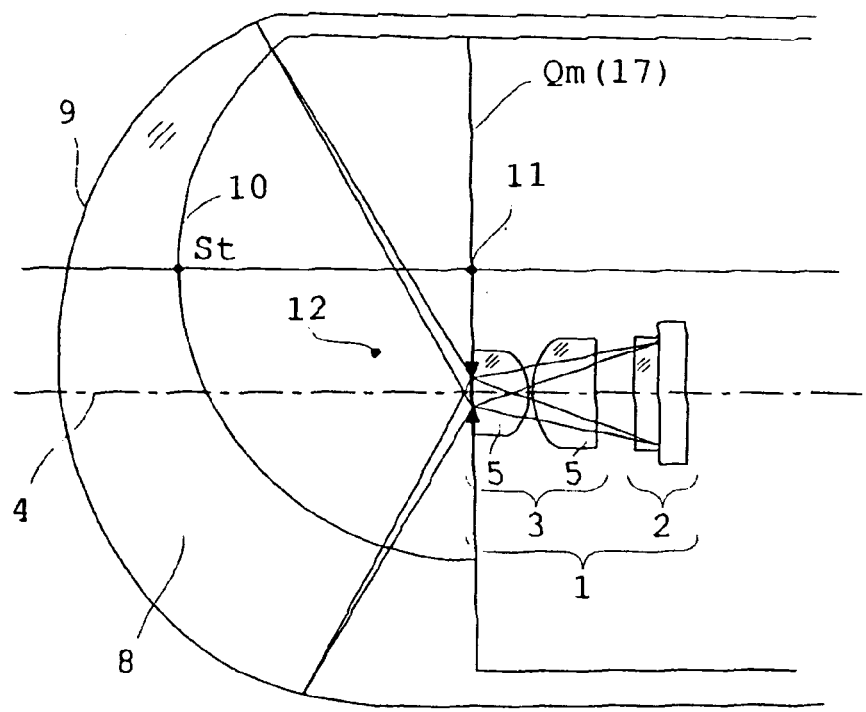
FIG. 18 relates to Embodiment 4 of the present invention, and illustrates the imaging of object points that are on the outer surface of the transparent cover at the outer limits of the field of view of the objective optical system.

FIG. 18 shows the front portion of a capsule-type endoscope according to Embodiment 4 of the present invention and is for explaining the image-formation of an object point on the outer surface 9 of the transparent cover 8 at the outer limits of the field of view of the objective optical system 3 for this embodiment. The plane of the figure is a cross-section that contains the optical axis 4 of the objective optical system 3 and the vertex St of the inner surface 10 of the transparent cover 8. The capsule-type endoscope of Embodiment 4 is different from that of Embodiment 3 in that focal shifts on the image plane caused by differences in the object point distances as measured from the outer surface 9 of the transparent cover 8 in different viewing directions are corrected without having to tilt the image pickup element. In this embodiment, the center of the field of view of the objective optical system 3 is positioned off the longitudinal axis of the capsule. In the capsule-type endoscope of Embodiment 4, the outer surface 9 of the transparent cover 8 is approximately symmetrically situated about the optical axis 4 of the objective optical system 3, and the vertex St of the inner surface of the transparent cover is offset from the optical axis 4 of the objective optical system 3. Moreover, the outer surface 9 of the transparent cover 8 is spherical in shape. The distance between the center of curvature 12 of the outer surface 9 of the transparent cover 8 and the optical axis 4 of the objective optical system is 0.4 mm. With this structure, focal shifts on the image plane caused by differences in the object point distance when the object point is positioned on the outer surface 9 of the transparent cover 8 in different viewing directions are not significant and can be corrected without having to tilt the image pickup element.

Embodiment 5

Figures 19A, 19B:
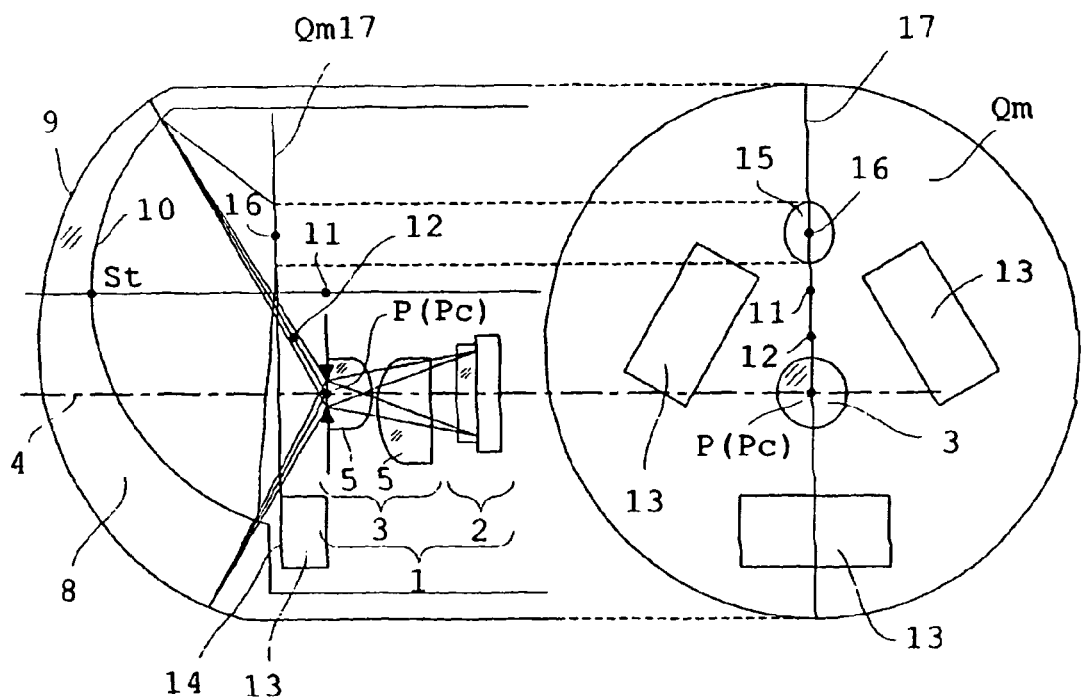
FIGS. 19(a) and 19(b) relate to Embodiment 5 of the present invention, with FIG. 19(a) being a cross-section of a front portion of the capsule-type endoscope as viewed from the side, and FIG. 19(b) being a cross-section of a front portion of the capsule-type endoscope as viewed from the front.

FIGS. 19(a) and 19(b) show the front portion of a capsule-type endoscope according to Embodiment 5 of the present invention, with FIG. 19(a) being a cross section (of a front portion of the capsule-shaped endoscope as viewed from the side) that contains the optical axis 4 of the objective optical system 3 and the vertex St of the inner surface 10 of the transparent cover 8, and FIG. 19(b) being a cross-section of a front portion of the capsule-shaped endoscope as viewed from the front. FIG. 19(a) illustrates forming images of object points on the outer surface 9 of the transparent cover 8 at the outer limits of the field of view of the objective optical system 3. FIG. 19(b) shows the positional relationships, within a plane Qm that contains the light emitting surface(s) of the illumination light source(s) that form an illumination means, of the centers of curvature 11 and 12 of the inner and outer surfaces 10 and 9, respectively, of the transparent cover 8 and the reflected image range 15 (as defined previously) of the entrance pupil of the objective optical system. In the capsule-type endoscope of Embodiment 5, the center of curvature 12 of the outer surface 9 of the transparent cover 8 (which lies on the longitudinal axis of the capsule) is offset relative to the optical axis 4 of the objective optical system, as well as relative to the center of curvature 11 of the inner surface 10 of the transparent cover 8, and one of the optical elements 5, 5 forming the objective optical system 3 is de-centered in order to compensate for object points at the outer surface of the transparent cover in different viewing directions being at different object distances from the entrance pupil of the objective optical system. Thus, focal shifts on the image plane caused by differences in the object point distances to the outer surface 9 of the transparent cover 8 in different viewing directions can be corrected even if the center of the field of view of the objective optical system 3 is positioned away from the longitudinal axis of the capsule.

Embodiment 6

Figures 20A, 20B:
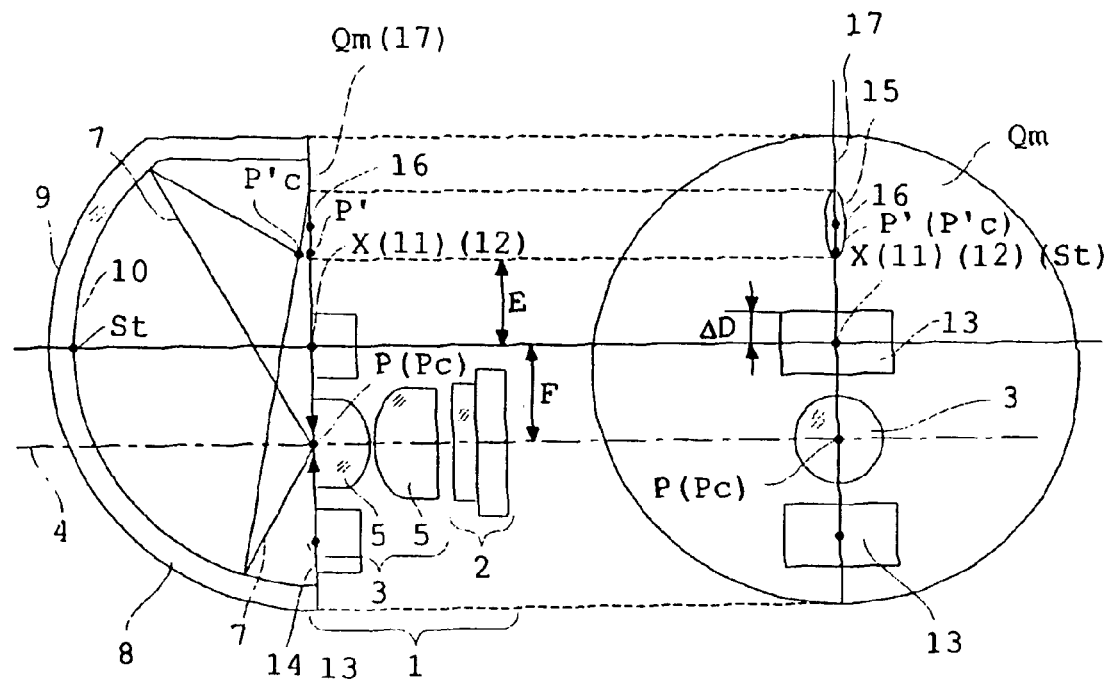
FIGS. 20(a) and 20(b) relate to Embodiment 6 of the present invention, with FIG. 20(a) being a cross-section of a front portion of the capsule-type endoscope as viewed from the side, and FIG. 20(b) being a cross-section of a front portion of the capsule-type endoscope as viewed from the front.

FIGS. 20(a) and 20(b) show cross sections of the front portion of a capsule-type endoscope according to Embodiment 6 of the present invention, with FIG. 20(a) illustrating a cross section that contains the optical axis 4 of the objective optical system 3 and the vertex St of the inner surface 10 of the transparent cover 8 as viewed from the side, and FIG. 20(*b*) illustrating a cross-section as viewed from the front. FIG. 20(*a*) illustrates forming images of object points on the outer surface 9 of the transparent cover 8 at the outer limits of the field of view of the objective optical system 3. FIG. 20(*b*) shows the positional relationships, within a plane Qm that contains the light emitting surfaces of the light sources that form the illumination means 13, of the centers of curvature 11 and 12 of the inner and outer surfaces 10 and 9, respectively, of the transparent cover 8 and the reflected image range 15 (as defined previously) of the entrance pupil of the objective optical system.

The inner surface 10 of the transparent cover 8 of Embodiment 6 is spherical. The center of curvature 11 of the inner surface 10 of the transparent cover 8 is on a line 17 that passes through the center Pc of the entrance pupil of the objective optical system 3 and is orthogonal to the optical axis 4 of the objective optical system 3. The entrance pupil of the objective optical system 3 coincides with the most object-side surface of the lenses 5, 5 that form the objective optical system 3. The objective optical system 3 is positioned so that the entrance pupil plane thereof is in the same plane as the plane Qm that contains the light emitting surfaces 14 of the illumination light sources that form the illumination means 13.

In order to provide uniform illumination within the field of view of the objective optical system 3 in the present invention, the illumination light sources that form the illumination means 13 are evenly positioned around the optical axis of the objective optical system. Preferably, the following Condition (7) is satisfied:

$$PX > (\phi L/2) + (\Delta D) \qquad \text{Condition (7)}$$

where

PX is the distance, on the plane Qm, between the intersection points P and X, where P is the intersection with the plane Qm of the optical axis of the objective optical system, and X is the intersection with the plane Qm of a line drawn from the vertex St of the inner surface of the transparent cover that is perpendicular to the plane Qm;

$\phi L$ is the outer diameter of the most object-side lens component of the objective optical system; and $\Delta D$ is the smallest distance between the center of an illumination light source and its outer periphery.

In the capsule-type endoscope of Embodiment 6, $\phi L = 0.75$ mm and $\Delta D = 0.55$ mm; therefore the distance between the intersection points P and X is 1.65 mm. This embodiment realizes a small-sized, capsule-type endoscope despite there being multiple illumination light sources that form the illumination means 13 so as to assure a sufficient brightness of illumination while simultaneously preventing light emitted from an illumination light source and reflected by the inner surface 10 of the transparent cover 8 from entering the entrance pupil of the objective optical system 3, thereby preventing flare.

Embodiment 7

Figures 21A, 21B:
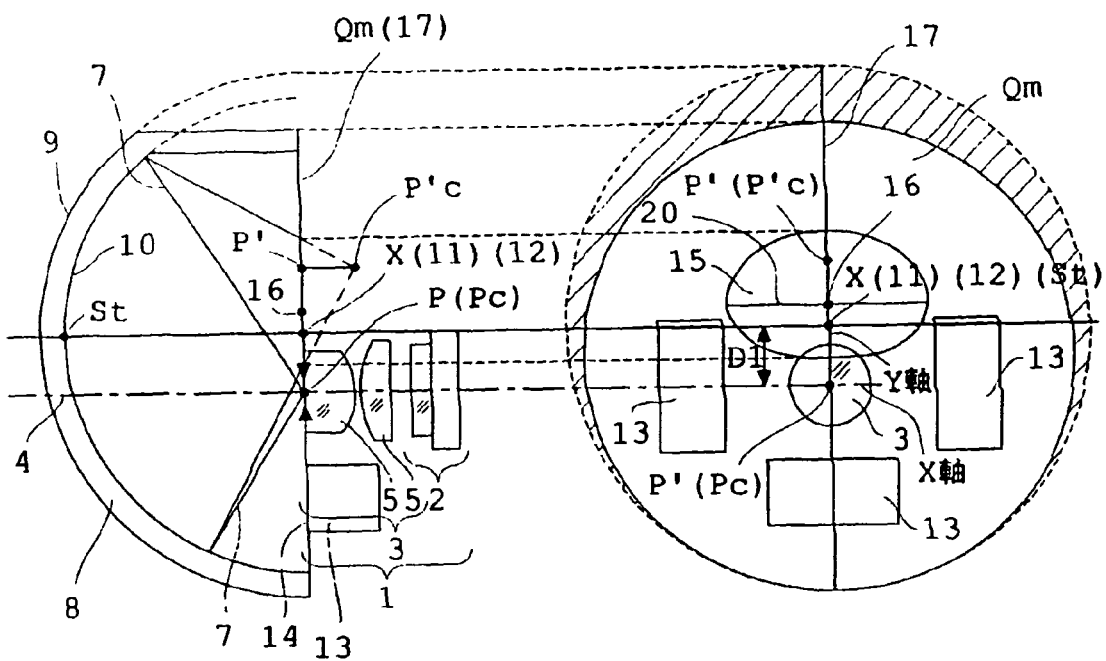
FIGS. 21(a) and 21(b) relate to Embodiment 7 of the present invention, with FIG. 21(a) being a cross-section of a front portion of the capsule-type endoscope as viewed from the side, and FIG. 21(b) being a cross-section of a front portion of the capsule-type endoscope as viewed from the front.

FIGS. 21(*a*) and 21(*b*) show cross sections of the front portion of a capsule-type endoscope according to Embodiment 7 of the present invention, with FIG. 21(*a*) illustrating a cross section that contains the optical axis 4 of the objective optical system 3 and the vertex St of the inner surface 10 of the transparent cover 8 as viewed from the side, and FIG. 21(*b*) illustrating a cross-section as viewed from the front. FIG. 21(*a*) illustrates forming images of object points on the outer surface 9 of the transparent cover 8 at the outer limits of the field of view of the objective optical system 3. FIG. 21(*b*) shows the positional relationships, within the plane Qm that contains the light emitting surfaces of the illumination light sources that form the illumination means, among the points St, Pc and P'c and the reflected image range 15 (all as defined previously) of the entrance pupil of the objective optical system.

The inner and outer surfaces 10 and 9 of the transparent cover 8 in the capsule-type endoscope of Embodiment 7 are both ellipsoidal. The inner surface 10 is defined by the following equation:

$$(x^2/4.96^2) + (y^2/5.55^2) = 1 \qquad \text{Equation (B)}$$

where x and y are the coordinates of the inner surface.

The coordinates of the focal points $(0, \pm 2.48)$ of the ellipsoidal transparent cover 8 are provided such that the center 11 of the inner surface 10 is the origin. The center 11 of the inner surface 10 is the center of the ellipsoid and is positioned at the intersection of the major and minor axes of the ellipsoid.

With the structure above, the reflected image range 15 of the entrance pupil of the objective optical system 3 projected via the inner surface 10 of the transparent cover 8 is as shown in FIG. 21(*b*). Three LEDs, that each comprise an illumination source of the illumination means 13, are positioned around the optical axis of the objective optical system 3 outside the reflected image range 15 (as defined previously). The center 16 of the reflected image range 15 is positioned along a line 17 in the plane Qm that connects the points P(Pc) and X, where P and X are as defined above. With the capsule-type endoscope of Embodiment 7, the outer diameter of the capsule can be reduced from 12 mm, as in a prior art capsule-type endoscope, to 10.85 mm (as shown by the hatched area in FIG. 21(*b*)).

As is apparent from the endoscope of Embodiment 7, the capsule-type endoscope of the present invention prevents light that is emitted by the illumination means 13 and reflected by the inner surface 10 of the transparent cover 8 from reaching the entrance pupil of the objective optical system 3, thus preventing flare even though the inner surface 10 of the transparent cover 8 is ellipsoidal in shape, while providing a small-sized, capsule-type endoscope that provides clear images.

When the inner surface 10 of the transparent cover 8 is ellipsoidal in shape, a coordinate system can be established with the origin at the center Pc of the entrance pupil of the objective optical system 3, with the y-axis being along the line that connects the center Pc of the entrance pupil of the objective optical system and the center of curvature 11 of the inner surface 10 of the transparent cover 8, and the x-axis being along the line that passes through the center Pc of the entrance pupil of the objective optical system 3 and is orthogonal to the y-axis. The positive direction of the y-axis is in the direction from the origin to the center of curvature 11 of the inner surface 10 of the transparent cover 8. Then, primary light 7 around the outermost peripheries of the field of view will be reflected by the inner surface 10 of the transparent cover 8 and will reach the x-y plane, with the y-coordinate being positive when the following Condition (8) is satisfied:

$$D1 > (\beta 1)2/(4 \cdot \alpha 1) \qquad \text{Condition (8)}$$

where $\beta 1$ equals the minor diameter of the ellipsoid divided by 2, and $\alpha 1$ equals the major diameter of the ellipsoid divided by 2.

Therefore, if the center coordinates of the light emitting surfaces of the illumination means 13 have y>0 on the x-y plane, light emitted from the illumination light sources of the illumination means 13 and reflected by the inner surface 10 of the transparent cover 8 will not enter the entrance pupil of the objective optical system 3, thereby preventing flare.

Figure 24:
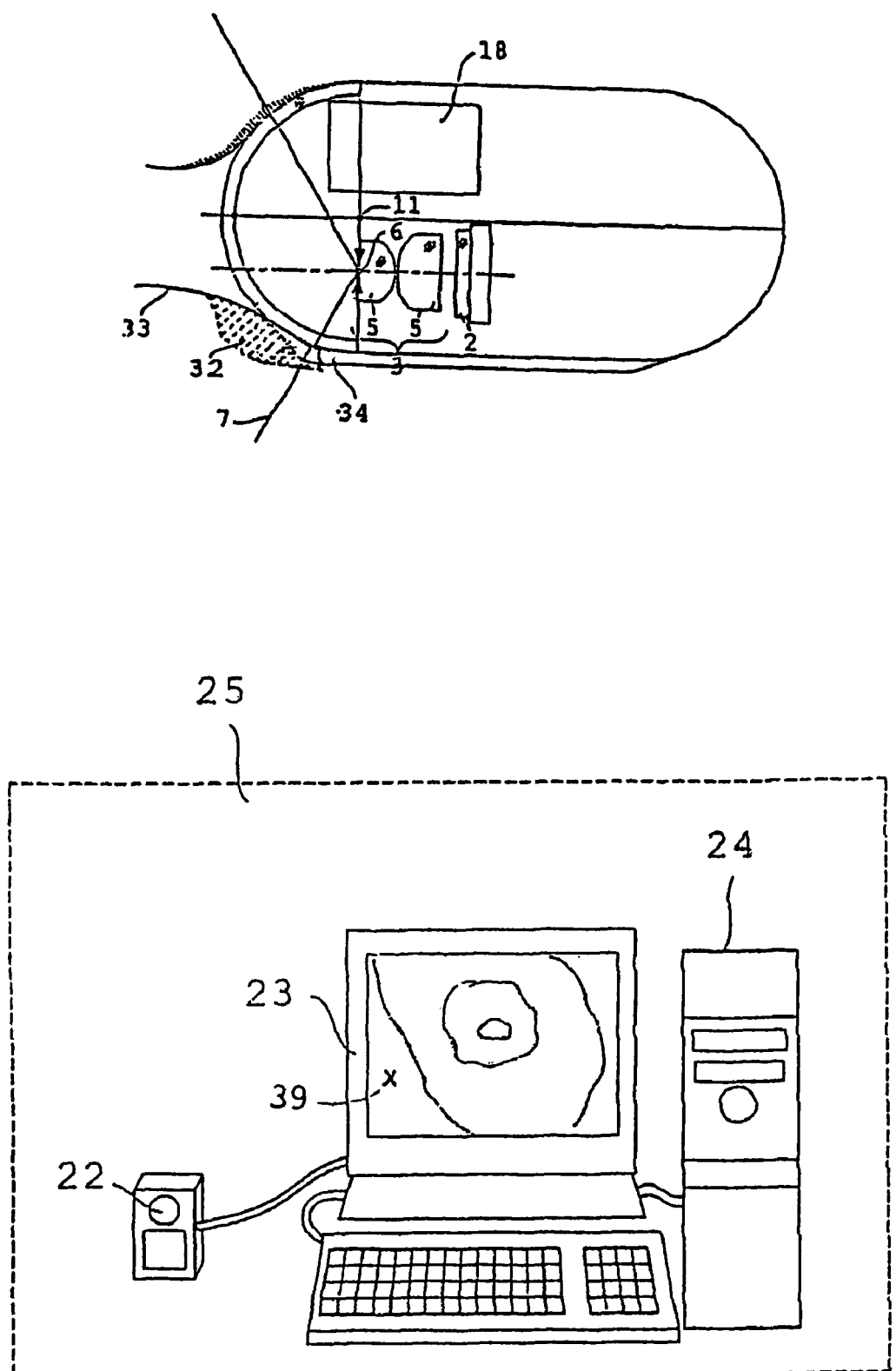
FIG. 24 is an illustration to explain a capsule-type endoscope system in which a marking can be displayed by analyzing the position where the tip of the puncture needle will make contact with a living tissue surface, based on the positional relationship between the puncture needle projection port, the living tissue, and the moving direction of the puncture needle.

FIG. 24 is an illustration to explain a capsule-type endoscope system in which a marking can be displayed by analyzing the position where the tip of the puncture needle makes contact with a living tissue surface, based on the positional relationship between the puncture needle projection port, the living tissue, and the moving direction of the puncture needle.

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. A capsule-type endoscope comprising:
    a capsule;
    an image pickup unit that includes an objective optical system having an optical axis and a field of view, and an image pickup element;
    an illumination light source having a light emitting surface; and
    a transparent cover that seals the objective optical system, the image pickup unit, and the illumination light source within the capsule;
wherein
    the light emitting surface of the illumination light source, which is planar, is positioned in such a manner that it does not overlap any part of an image of the entrance pupil of the objective optical system, said image being defined when hypothetical light rays emitted from the center of the entrance pupil at the outer limits of the field of view of the objective optical system are projected onto a plane Qm by being reflected by the inner surface of the transparent cover, where the plane Qm is the plane containing the light emitting surface of the illumination light source;
    an inner surface of the transparent cover is spherical within the field of view of the objective optical system so as to have a center of curvature, the center of curvature is offset from the optical axis of the objective optical system, and the following condition is satisfied:

$$0.01 < L1/R \tan\theta < 0.5$$

where
    L1 is the distance between the center of curvature of the inner surface of the transparent cover and the optical axis of the objective optical system;
    R is the radius of curvature of the inner surface of the transparent cover; and
    θ is the half-field angle of the objective optical system.

2. The capsule-type endoscope according to claim 1, wherein the objective optical system satisfies the following conditions:

$$R1 \geq 5 \text{ lines per mm}$$

$$R2 \geq 1 \text{ line per mm}$$

where
    R1 is the resolution on the optical axis at positions between the most object-side surface of the objective optical system and the point of intersection of the optical axis of the objective optical system with an outer surface of the transparent cover; and
    R2 is the resolution on the optical axis at positions between the most object-side surface of the objective optical system and a far point of the depth of field of the objective optical system.

3. The capsule-type endoscope according to claim 2, wherein the image pickup unit satisfies the following conditions:

$$80 < IH/P < 500$$

$$80 < FL/P < 500$$

$$400 < Fno/P < 3000$$

where
    IH is the distance, in mm, between the center and the furthermost point of the effective image pickup area of the light receiving surface of the image pickup element;
    P is the horizontal pixel pitch, in mm, of the image pickup element;
    FL is the focal length, in mm, of the objective optical system; and
    Fno is the effective F-number of the objective optical system.

4. The capsule-type endoscope according to claim 1, wherein:
    at least one optical component of the image pickup unit is de-centered relative to other components of the image pickup unit.

5. The capsule-type endoscope according to claim 1, wherein an outer surface of the transparent cover is spherical and within 0.4 mm of being symmetric about the optical axis of the objective optical system.

6. A capsule-type endoscope comprising:
    a capsule;
    an image pickup unit that includes an objective optical system having an optical axis and a field of view, and an image pickup element;
    an illumination light source having a light emitting surface;
    a transparent cover that seals the objective optical system, the image pickup unit, and the illumination light source within the capsule;
    a tank that is located within the capsule; and
    a nozzle, that is located outside the capsule, for spraying a substance carried in the tank; wherein
    the nozzle is located at a position and orientation that is outside the field of view of the objective optical system, but the field of view of the objective optical system and a spray range of the nozzle overlap;
    an inner surface of the transparent cover is spherical within the field of view of the objective optical system so as to have a center of curvature, the center of curvature is offset from the optical axis of the objective optical system; and
    the following condition is satisfied:

$$0.01 < L1/R \tan\theta < 0.5$$

where
    L1 is the distance between the center of curvature of the inner surface of the transparent cover and the optical axis of the objective optical system;
    R is the radius of curvature of the inner surface of the transparent cover; and
    θ is the half-field angle of the objective optical system.

7. The capsule-type endoscope according to claim 6, wherein the nozzle is oriented so that the following condition is satisfied:

$$15° \leq \beta \leq 75°$$

where

β is the angle between the optical axis of the objective optical system and a centerline of an orifice of the nozzle.

8. The capsule-type endoscope according to claim 6, wherein:
the nozzle is connected to the tank through the transparent cover at a location that is outside the field of view of the objective optical system.

9. The capsule-type endoscope according to claim 6, wherein the nozzle and the tank are detachably attached to the capsule.

10. A capsule-type endoscope that includes an image pickup unit, said capsule-type endoscope comprising an objective optical system, an image pickup element, and at least one illumination light source located at different positions within a capsule that has a transparent cover that seals these items within the capsule,
wherein
at least within the field of view of the objective optical system, the inner surface of the transparent cover is spherical;
light-emitting surface(s) of the illumination light source(s) does(do) not overlap with an image of the entrance pupil of the objective optical system that is projected onto a plane Qm by light rays that are reflected by the inner surface of the transparent cover; and
X lies on a line drawn from P to P'
where
Qm is a plane that contains the light-emitting surface(s) of the illumination light source(s);
X is the point of intersection with the plane Qm of a line drawn from the vertex St of the inner surface of the transparent cover so as to be normal to the plane Qm;
P is the point of intersection with the plane Qm of a line that is drawn from the center of the entrance pupil of the objective optical system so as to be perpendicular to the plane Qm;
P' is the point of intersection with the plane Qm of a line that is drawn from a point P'c so as to be normal to the plane Qm; and
P'c is the point of intersection of hypothetical light rays emitted from the center of the entrance pupil of the objective optical system after such light rays are reflected by the inner surface of the transparent cover at positions that are at the outer limits of the field of view of the objective optical system in a cross section that contains the vertex of the inner surface of the transparent cover and the optical axis of the objective optical system.

11. The capsule-type endoscope according to claim 10, wherein:
a tank is further provided inside the capsule;
a nozzle, for spraying a substance carried in the tank, is provided outside the capsule; and
the nozzle is provided at a position that is outside the field of view of the objective optical system but where the field of view of the objective optical system and a spray range of the nozzle overlap.

12. The capsule-type endoscope according to claim 11, wherein the nozzle is oriented so that the following condition is satisfied:

$$15° \leq \beta \leq 75°$$

where

β is the angle between the optical axis of the objective optical system and the centerline of an orifice of the nozzle.

13. The capsule-type endoscope according to claim 11, wherein the nozzle is connected to the tank through the transparent cover at a location that is outside the field of view of the objective optical system.

14. The capsule-type endoscope according to claim 11, wherein the nozzle and the tank are detachably attached to the capsule.

15. The capsule-type endoscope according to claim 10, wherein at least one of the components of the image pickup unit is tilted so as to be non-orthogonal to the optical axis of the objective optical system or is de-centered relative to other components of the image pickup unit.

16. The capsule-type endoscope according to claim 10, wherein:
the outer surface of the transparent cover is spherical and within 0.4 mm of being symmetric about the optical axis of the objective optical system.

17. The capsule-type endoscope according to claim 10, wherein:
a puncture needle and a mechanism for pushing the puncture needle outside the capsule are further provided inside the capsule;
a projection port for the puncture needle is provided on an exterior surface of the capsule; and
the projection port is located at a position that is outside the field of view of the objective optical system but, when the puncture needle is projected through the projection port, the tip of the puncture needle comes within the field of view of the objective optical system before it makes contact with a puncture target region.

18. The capsule-type endoscope according to claim 17, wherein the projection port passes through the transparent cover at a location that is outside the field of view of the objective optical system.

19. The capsule-type endoscope according to claim 17, wherein a puncture-needle storage part that includes the projection port is detachably attached to the capsule.

20. The capsule-type endoscope according to claim 10, wherein:
a tank is further provided inside the capsule;
a nozzle, for spraying a substance carried in the tank, is provided outside the capsule; and
at least a portion of the nozzle is positioned within the field of view of the objective optical system.

21. The capsule-type endoscope according to claim 20, wherein the nozzle is oriented so that the following condition is satisfied:

$$15° \leq \beta \leq 75°$$

where

β is the angle between the optical axis of the objective optical system and the centerline of an orifice of the nozzle.

22. The capsule-type endoscope according to claim 20, wherein the nozzle is connected to the tank through the transparent cover at a location such that the nozzle is outside the field of view of the objective optical system.

23. The capsule-type endoscope according to claim 20, wherein the nozzle and the tank are detachably attached to the capsule.

24. The capsule-type endoscope according to claim 10, wherein the objective optical system satisfies the following conditions:

$$R1 \geq 5 \text{ lines per mm}$$

$$R2 \geq 1 \text{ line per mm}$$

where
- R1 is the resolution on the optical axis at positions between the most object-side surface of the objective optical system and the point of intersection of the optical axis of the objective optical system with an outer surface of the transparent cover; and
- R2 is the resolution on the optical axis at positions between the most object-side surface of the objective optical system and a far point of the depth of field of the objective optical system.

25. The capsule-type endoscope according to claim 24, wherein the image pickup unit satisfies the following conditions:

$$80 < IH/P < 500$$

$$80 < FL/P < 500$$

$$400 < Fno/P < 3000$$

where
- IH is the distance, in mm, between the center and the furthermost point of the effective image pickup area of the light-receiving surface of the image pickup element;
- P is the horizontal pixel pitch, in mm, of the image pickup element;
- FL is the focal length, in mm, of the objective optical system; and
- Fno is the effective F-number of the objective optical system.

\* \* \* \* \*